(12) United States Patent
Andreas et al.

(10) Patent No.: US 8,585,747 B2
(45) Date of Patent: Nov. 19, 2013

(54) DEVICES AND METHODS FOR CONTROLLING AND INDICATING THE LENGTH OF AN INTERVENTIONAL ELEMENT

(75) Inventors: Bernard Andreas, Redwood City, CA (US); Joseph Karratt, Millbrae, CA (US); James R. Flom, San Francisco, CA (US); Bradley Blackwood, San Jose, CA (US)

(73) Assignee: J.W. Medical Systems Ltd., Weihai Shangdong (CN)

( * ) Notice: Subject to any disclaimer, the term of this patent is extended or adjusted under 35 U.S.C. 154(b) by 48 days.

(21) Appl. No.: 11/953,242

(22) Filed: Dec. 10, 2007

(65) Prior Publication Data
US 2008/0091257 A1  Apr. 17, 2008

Related U.S. Application Data

(62) Division of application No. 10/746,466, filed on Dec. 23, 2003, now Pat. No. 7,326,236.

(51) Int. Cl.
*A61F 2/06* (2013.01)
(52) U.S. Cl.
USPC ........................................ 623/1.11; 623/1.12
(58) Field of Classification Search
USPC ................ 604/96.01, 97.01, 103.07, 103.08, 604/103.11, 916; 606/190–195, 198, 108; 623/1.11, 1.12, 1.23, 2.11
See application file for complete search history.

(56) References Cited

U.S. PATENT DOCUMENTS

| 4,069,825 A | 1/1978 | Akiyama |
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |

(Continued)

FOREIGN PATENT DOCUMENTS

| DE | 1 953 1659 | 3/1997 |
| DE | 1 963 0469 | 1/1998 |

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Ryan Severson
*Assistant Examiner* — David Eastwood
(74) *Attorney, Agent, or Firm* — Kilpatrick Townsend & Stockton LLP

(57) ABSTRACT

Devices and methods are provided for controlling and indicating the deployed length of an interventional element on an interventional catheter. The interventional element may be a stent or series of stents, a balloon, or any other interventional element for which length control is necessary or desirable. Devices for controlling the length of the interventional element include gear driven actuators, motors, and other mechanisms. Devices for indicating length of an interventional element to the user include sensors, detents, visual displays and other mechanisms providing visual, audible, and tangible indications of length to the user. The control and indication devices preferably work in tandem to enable highly precise adjustment of interventional element length.

52 Claims, 22 Drawing Sheets

(56) References Cited

U.S. PATENT DOCUMENTS

| | | | |
|---|---|---|---|
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |
| 5,282,823 A | 2/1994 | Schwartz et al. |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A * | 11/1998 | Poncet ........................ 623/1.11 |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A * | 8/1999 | Patterson et al. ............. 604/508 |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |

(56) References Cited

U.S. PATENT DOCUMENTS

| | | | |
|---|---|---|---|
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 * | 7/2003 | Gillick et al. ............ 606/108 |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 * | 9/2005 | Nicholas ............... 623/1.34 |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |

(56) References Cited

U.S. PATENT DOCUMENTS

| | | |
|---|---|---|
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,918,881 B2 | 4/2011 | Andreas et al. |
| 7,993,388 B2 | 8/2011 | Lee et al. |
| 8,257,427 B2 | 9/2012 | Andersen et al. |
| 8,317,850 B2 | 11/2012 | Kusleika |
| 2001/0001824 A1 | 5/2001 | Wu |
| 2001/0020154 A1 | 9/2001 | Bigus et al. |
| 2001/0020173 A1* | 9/2001 | Klumb et al. ........... 606/194 |
| 2001/0020181 A1 | 9/2001 | Layne |
| 2001/0035902 A1* | 11/2001 | Iddan et al. ............. 348/76 |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0032457 A1 | 3/2002 | Sirhan et al. |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1* | 7/2002 | LaFontaine et al. ........ 128/898 |
| 2002/0107560 A1* | 8/2002 | Richter ................. 623/1.11 |
| 2002/0111671 A1 | 8/2002 | Stenzel |
| 2002/0123786 A1* | 9/2002 | Gittings et al. ........... 623/1.11 |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1* | 10/2002 | Tran et al. ............. 623/1.12 |
| 2002/0156496 A1 | 10/2002 | Chermoni |
| 2002/0165599 A1 | 11/2002 | Nasralla |
| 2002/0168317 A1* | 11/2002 | Daighighian et al. ....... 424/1.11 |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1 | 6/2005 | Griffin |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |

(56) References Cited

U.S. PATENT DOCUMENTS

| | | |
|---|---|---|
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |

FOREIGN PATENT DOCUMENTS

| | | |
|---|---|---|
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 696 447 A2 | 2/1996 |
| EP | 0 714 640 | 6/1996 |
| EP | 0 797 963 A2 | 1/1997 |
| EP | 0 596 145 | 5/1997 |
| EP | 0 947 180 | 10/1999 |
| EP | 1 254 644 A1 | 11/2002 |
| EP | 1 258 230 A | 11/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 266 638 B1 | 10/2005 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2001-190687 | 7/2001 |
| JP | 2002-538932 T | 11/2002 |
| JP | 2004-121343 A | 4/2004 |
| WO | WO 94/27667 A1 | 12/1994 |
| WO | WO 95/26695 A2 | 10/1995 |
| WO | WO 95/29647 A2 | 11/1995 |
| WO | WO 96/26689 | 9/1996 |
| WO | WO 96/33677 | 10/1996 |
| WO | WO 96/37167 A1 | 11/1996 |
| WO | WO 96/39077 | 12/1996 |
| WO | WO 97/10778 | 3/1997 |
| WO | WO 97/46174 | 12/1997 |
| WO | WO 97/48351 | 12/1997 |
| WO | WO 98/20810 | 5/1998 |
| WO | WO 98/37833 | 9/1998 |
| WO | WO 98/58600 | 12/1998 |
| WO | WO 99/01087 | 1/1999 |
| WO | WO 99/65421 | 12/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | WO 00/51525 A1 | 9/2000 |
| WO | WO 00/56237 | 9/2000 |
| WO | WO 00/62708 | 10/2000 |
| WO | WO 00/72780 | 12/2000 |
| WO | WO 01/26707 | 4/2001 |
| WO | WO 01/34063 | 5/2001 |
| WO | WO 01/70297 | 9/2001 |
| WO | WO 01/91918 | 12/2001 |
| WO | 02/071975 | 9/2002 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | WO 2004/087006 | 10/2004 |
| WO | WO 2005/009295 | 2/2005 |
| WO | WO 2005/013853 | 2/2005 |
| WO | WO 2005/023153 | 3/2005 |
| WO | WO 2006/047520 | 5/2006 |
| WO | WO 2007/035805 | 3/2007 |
| WO | WO 2007/053187 | 5/2007 |
| WO | WO 2007/146411 | 12/2007 |
| WO | WO 2008/005111 | 1/2008 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

(56) References Cited

OTHER PUBLICATIONS

Stimpson et al., Parallel Production of Oligonucleotide Arrays Using Membranes and Reagent Jet Printing, BioTechniques 25:886-890 (Nov. 1998).
U.S. Appl. No. 60/336,607, filed Dec. 3, 2001, first named inventor: Bernard Andreas.
U.S. Appl. No. 60/336,767, filed Dec. 3, 2001, first named inventor: Bernard Andreas.
U.S. Appl. No. 60/336,967, filed Dec. 3, 2001, first named inventor: Sunmi Chew.
U.S. Appl. No. 60/364,389, filed Mar. 13, 2002, first named inventor: Sunmi Chew.
U.S. Appl. No. 60/440,839, filed Jan. 17, 2003, first named inventor: Bernard Andreas.
U.S. Appl. No. 60/561,041, filed Apr. 9, 2004, first named inventor: Jeffry Grainger.
U.S. Appl. No. 60/784,309, filed Mar. 20, 2006, first named inventor: Bernard Andreas.
U.S. Appl. No. 60/810,522, filed Jun. 2, 2006, first named inventor: Stephen Kaplan.
U.S. Appl. No. 60/890,703, filed Feb. 20, 2007, first named inventor: Patrick Ruane.
U.S. Appl. No. 61/012,317, filed Dec. 7, 2007, first named inventor: Patrick Ruane.
U.S. Appl. No. 09/097,855, filed Jun. 15, 1998, first named inventor: Enrique J. Klein.
U.S. Appl. No. 09/225,364, filed Jan. 4, 1999, first named inventor: Aaron V. Kaplan.
U.S. Appl. No. 10/874,859, filed Jun. 22, 2004, first named inventor: Pablo Acosta. Abandoned.
U.S. Appl. No. 11/462,951, filed Aug. 7, 2006, first named inventor: David Snow.
U.S. Appl. No. 11/627,096, filed Jan. 25, 2007, first named inventor: Bernard Andreas.
U.S. Appl. No. 11/689,927, filed Mar. 22, 2007, first named inventor: David Snow.
U.S. Appl. No. 11/752,448, filed May 23, 2007, first named inventor: David Snow.
U.S. Appl. No. 11/771,929, filed Jun. 29, 2007, first named inventor: David Snow.
U.S. Appl. No. 11/857,562, filed Sep. 19, 2007, first named inventor: Bryan Mao.
U.S. Appl. No. 11/938,730, filed Nov. 12, 2007, first named inventor: Sunmi Chew.
U.S. Appl. No. 11/945,142, filed Nov. 26, 2007, first named inventor: Bernard Andreas.
U.S. Appl. No. 11/947,677, filed Nov. 29, 2007, first named inventor: Dan Hammersmark.
U.S. Appl. No. 11/952,644, filed Dec. 7, 2007, first named inventor: Bernard Andreas.
U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
Supplementary European Search Report of EP Patent Application No. 05727731.1, dated Mar. 25, 2008, 2 pages total.
Supplementary European Search Report of EP Patent Application No. 05744136, dated Mar. 26, 2008, 3 pages total.
International Search Report and Written Opinion of PCT Application No. PCT/US2007/086864, mailed May 13, 2008, 16 pages.
U.S. Appl. No. 12/061,951, filed Apr. 3, 2008, first named inventor: Stephen Kao.
U.S. Appl. No. 12/109,477, filed Apr. 25, 2008, first named inventor: Stephen Kao.
U.S. Appl. No. 12/127,147, filed May 27, 2008, first named inventor: Sunmi Chew.
"Drug Delivery Stent With Holes Located on Neutral Axis" Research Disclosure, Kenneth Mason Publications, Hampshire, CB, No. 429, Jan. 2000, p. 13, XP00976354.
Office Action of Japanese Patent Application No. 2006-547139, mailed Jun. 15, 2010, 5 pages total. (English Translation Included).
Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.
Tilley, "Biolimus A9-Eluting Stent Shows Promise," Medscape Medical News, Oct. 5, 2004; retrieved from the Internet: <http://www.medscape.com/viewarticle/490621>, 2 pages total.
Weir et al., "Degradation of poly-L-lactide. Part 2: increased temperature accelerated degradation," Proc Inst Mech Eng H. 2004;218(5):321-30.
Supplementary European Search Report of EP Patent Application No. 07758831, dated Dec. 14, 2009.

\* cited by examiner

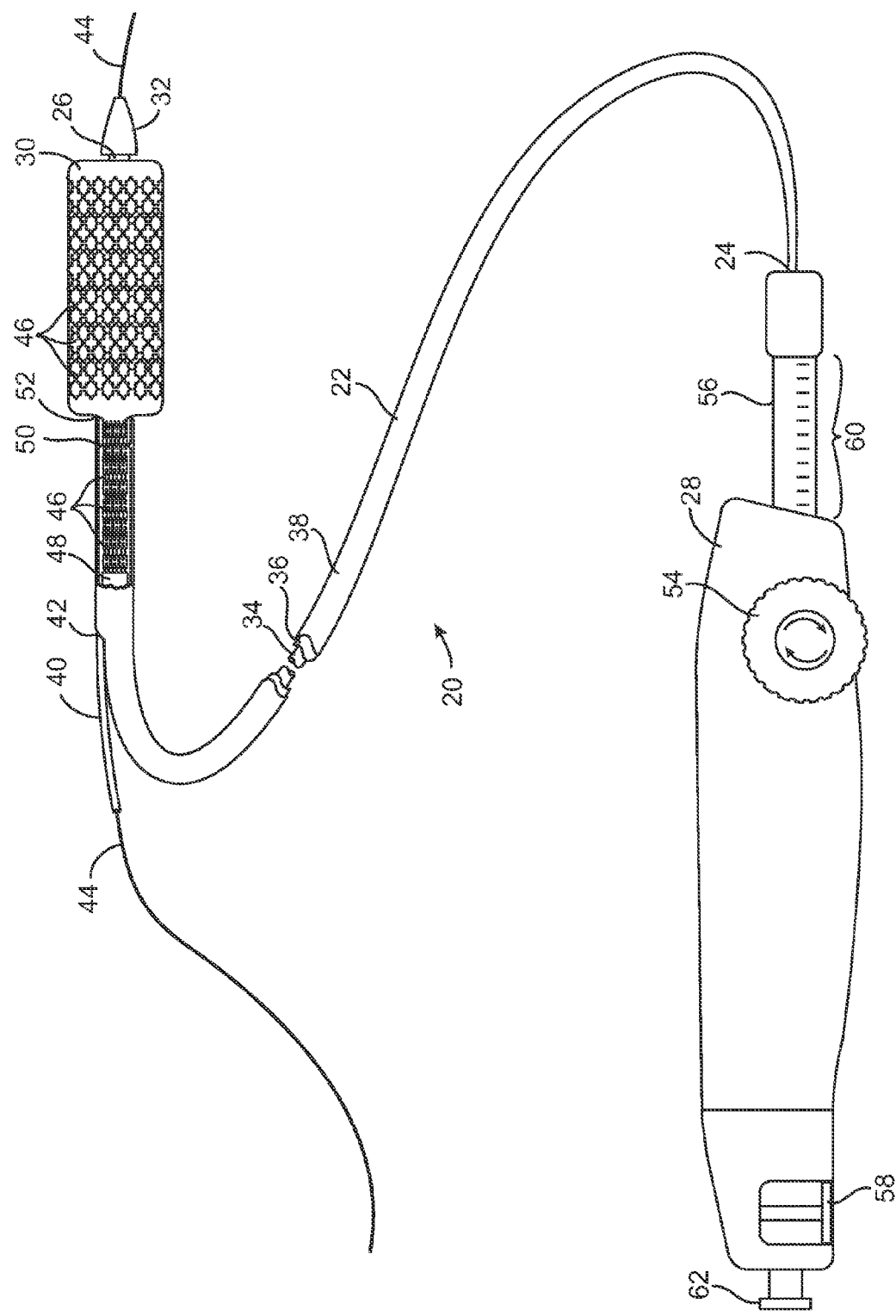

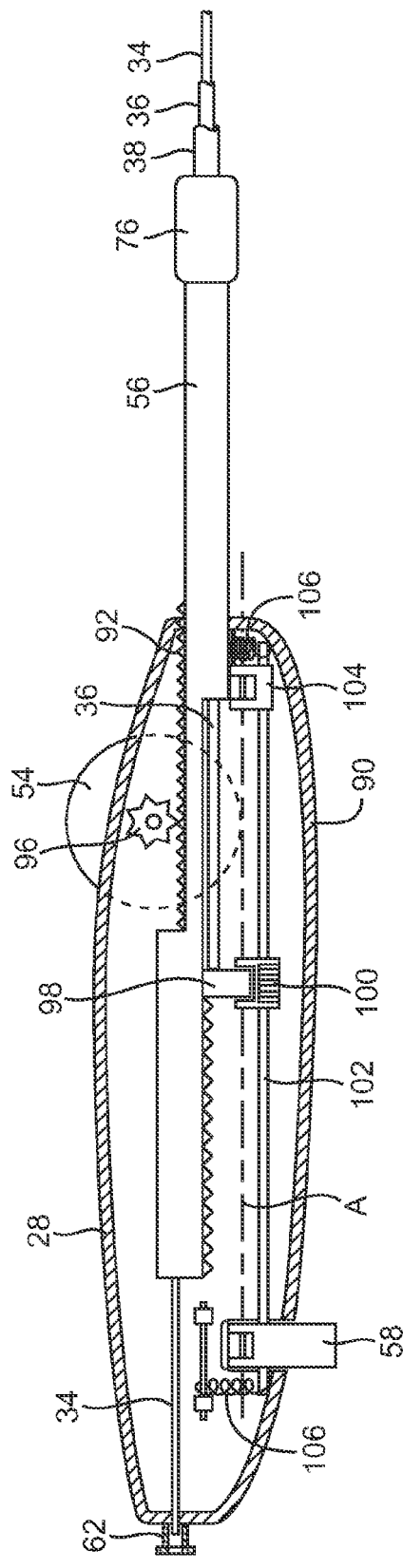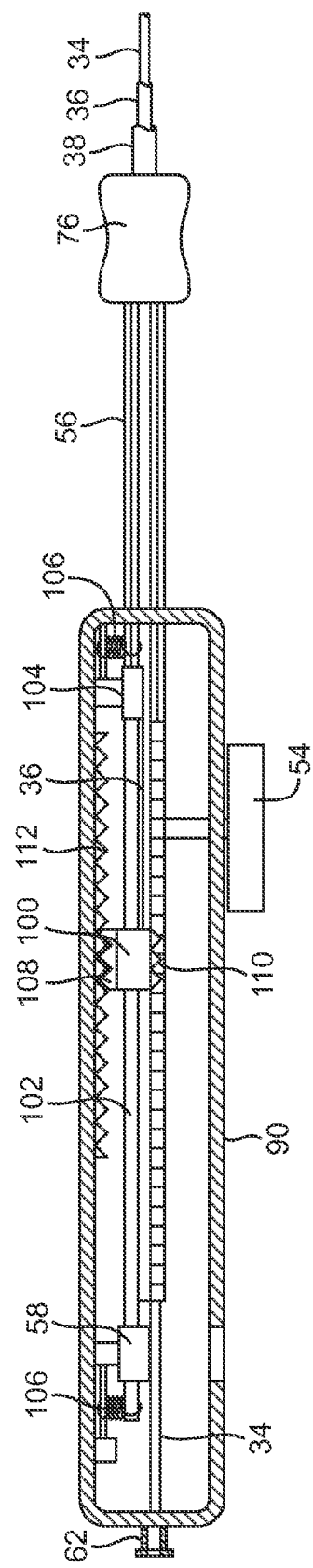

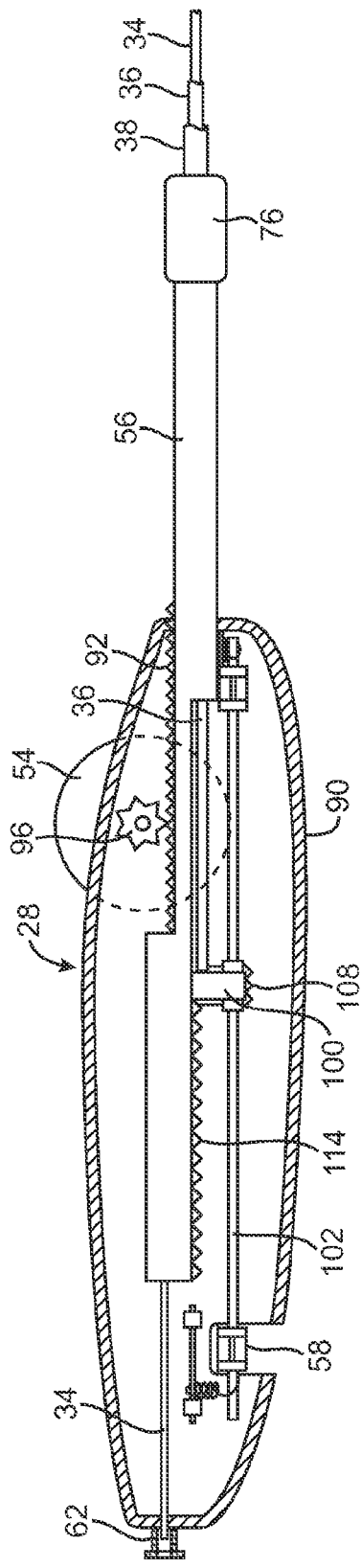
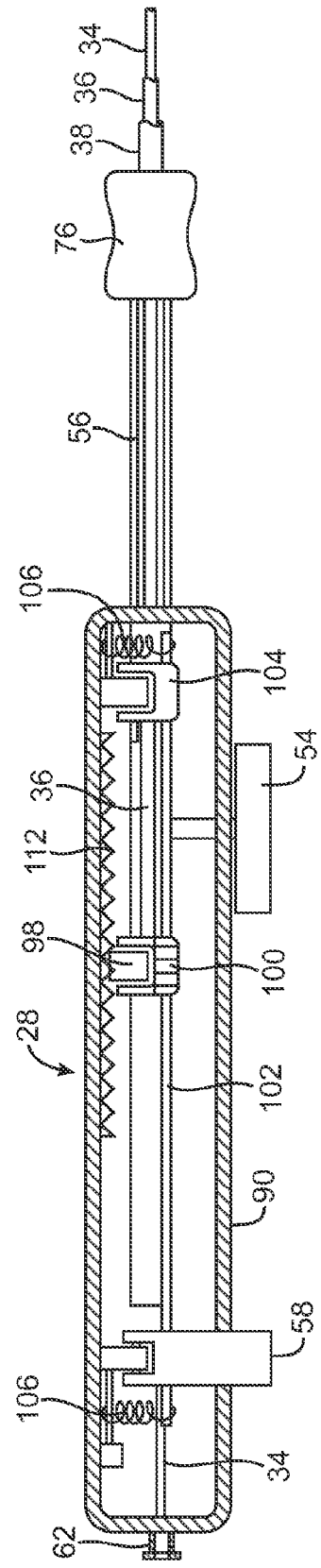
FIG. 7A
FIG. 7B

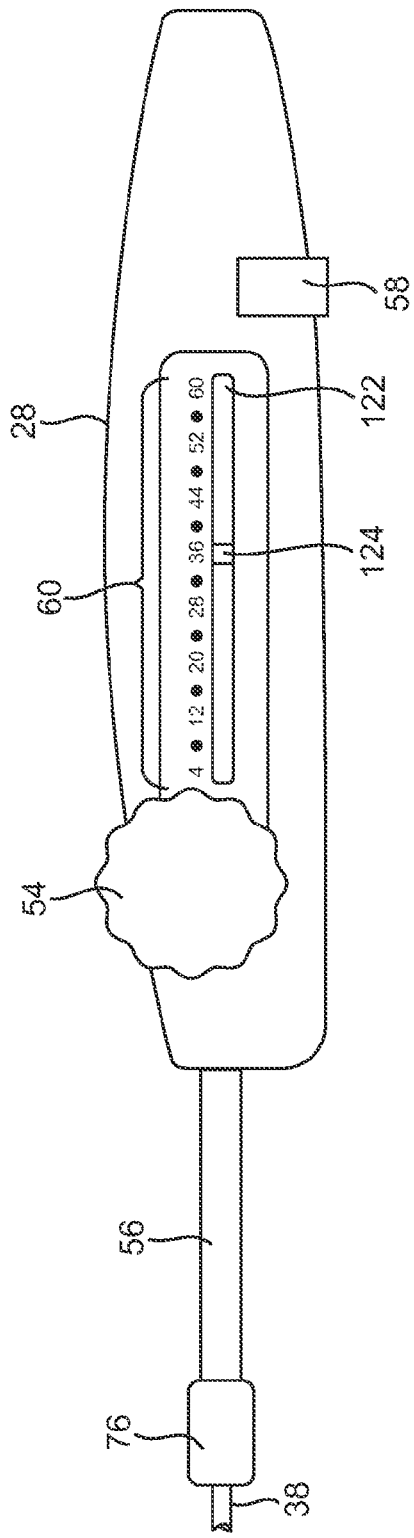
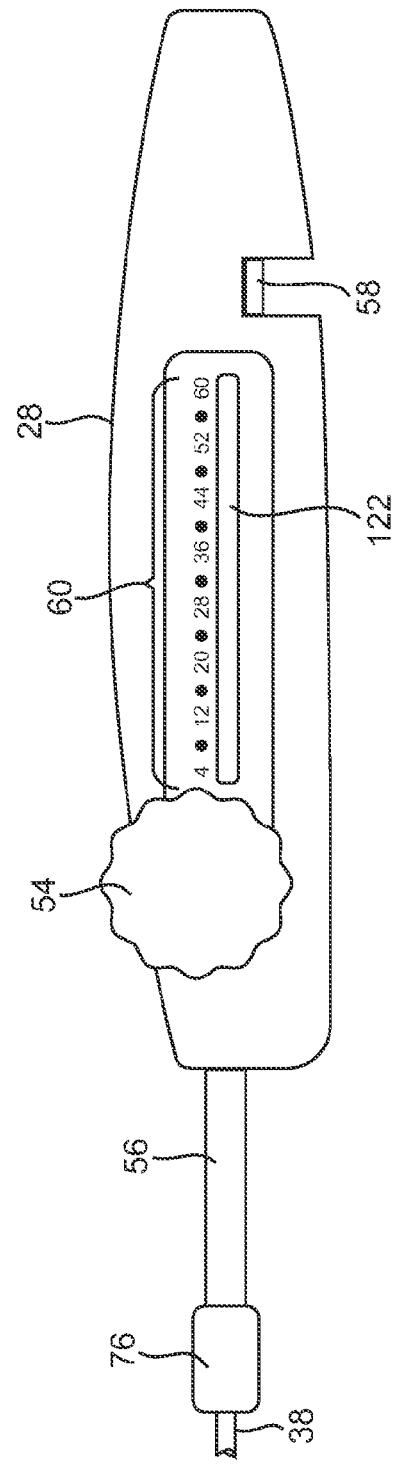

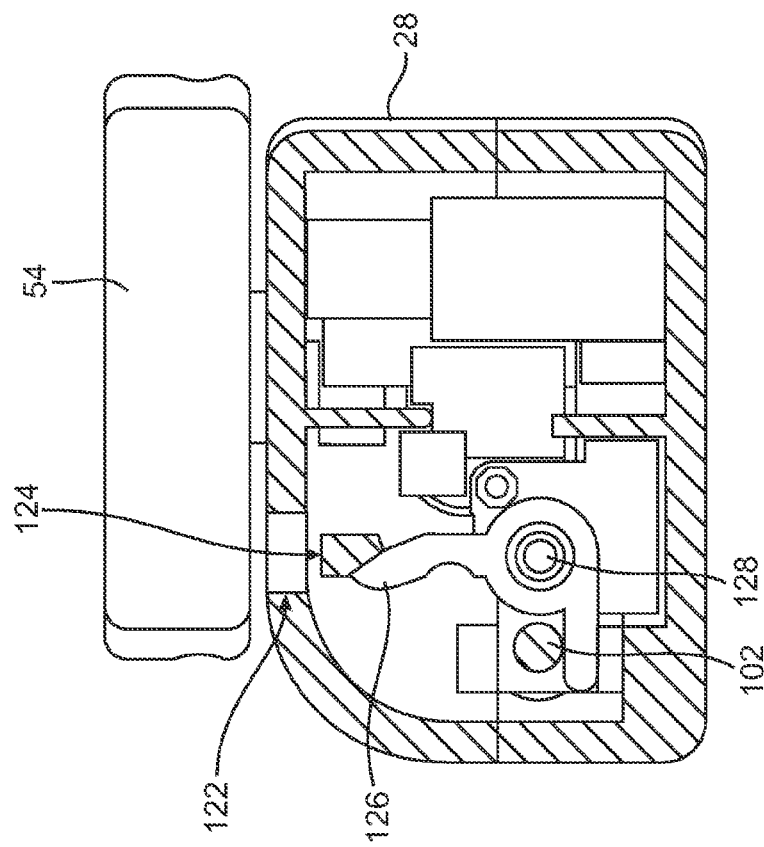
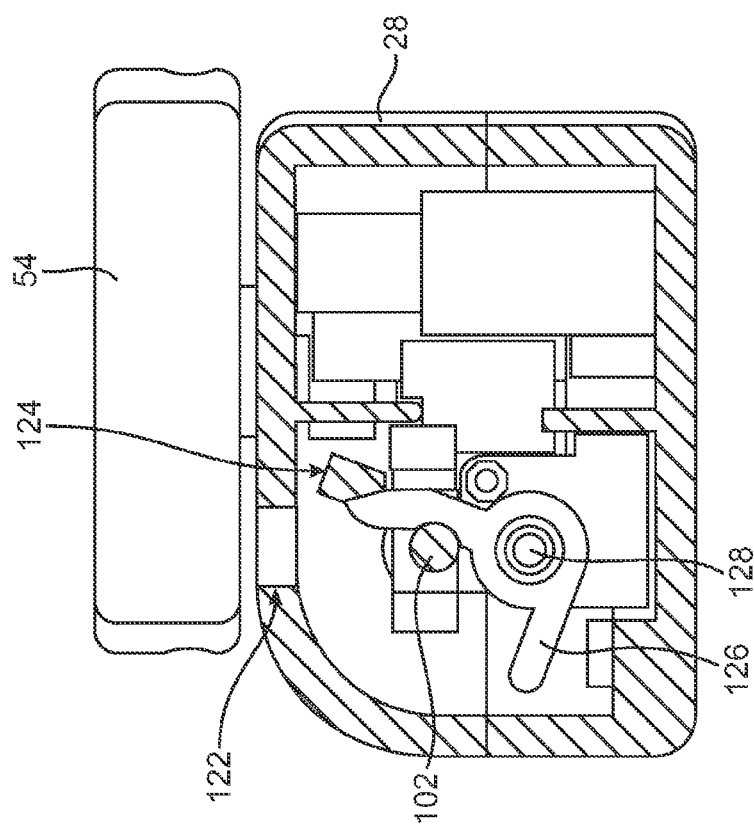

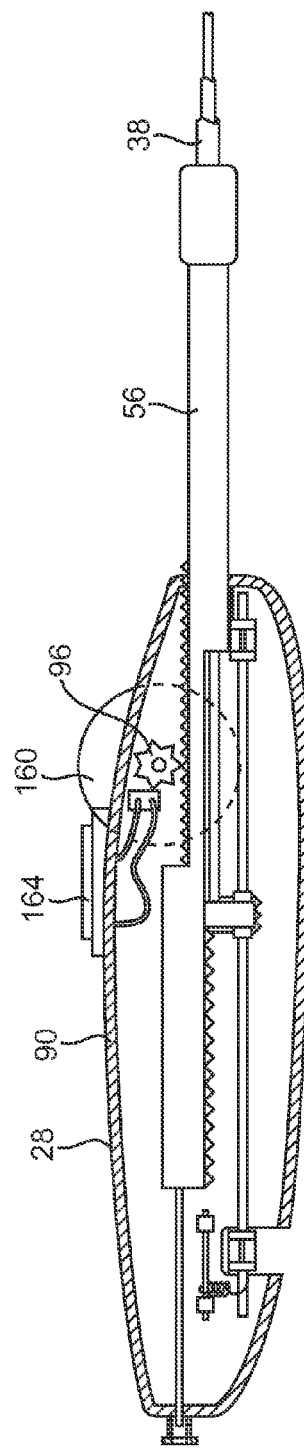
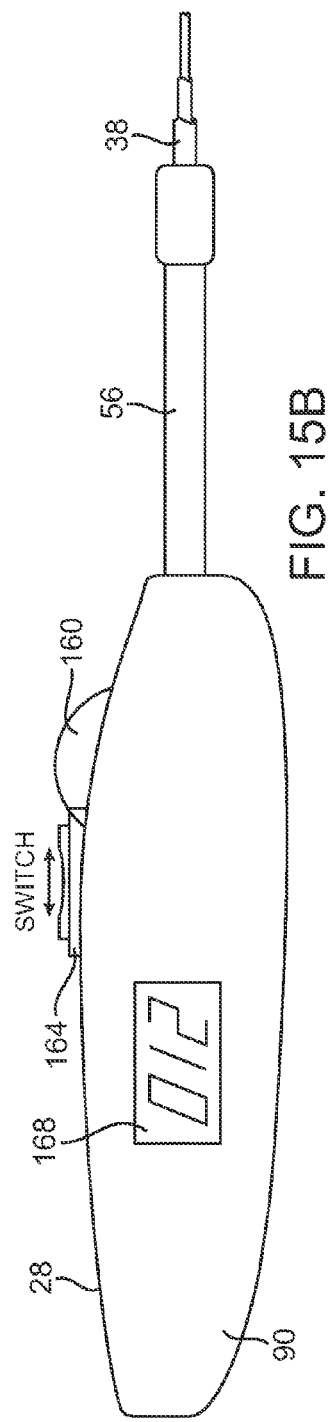
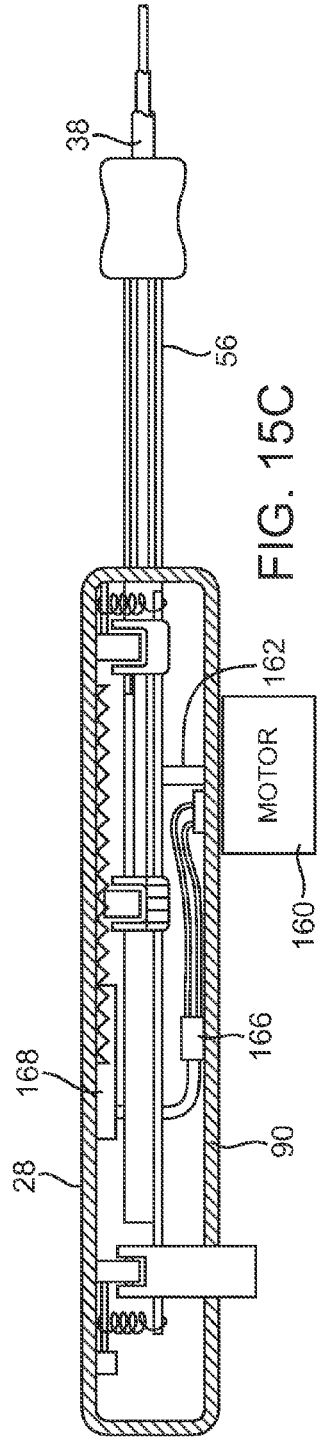
FIG. 15A
FIG. 15B
FIG. 15C

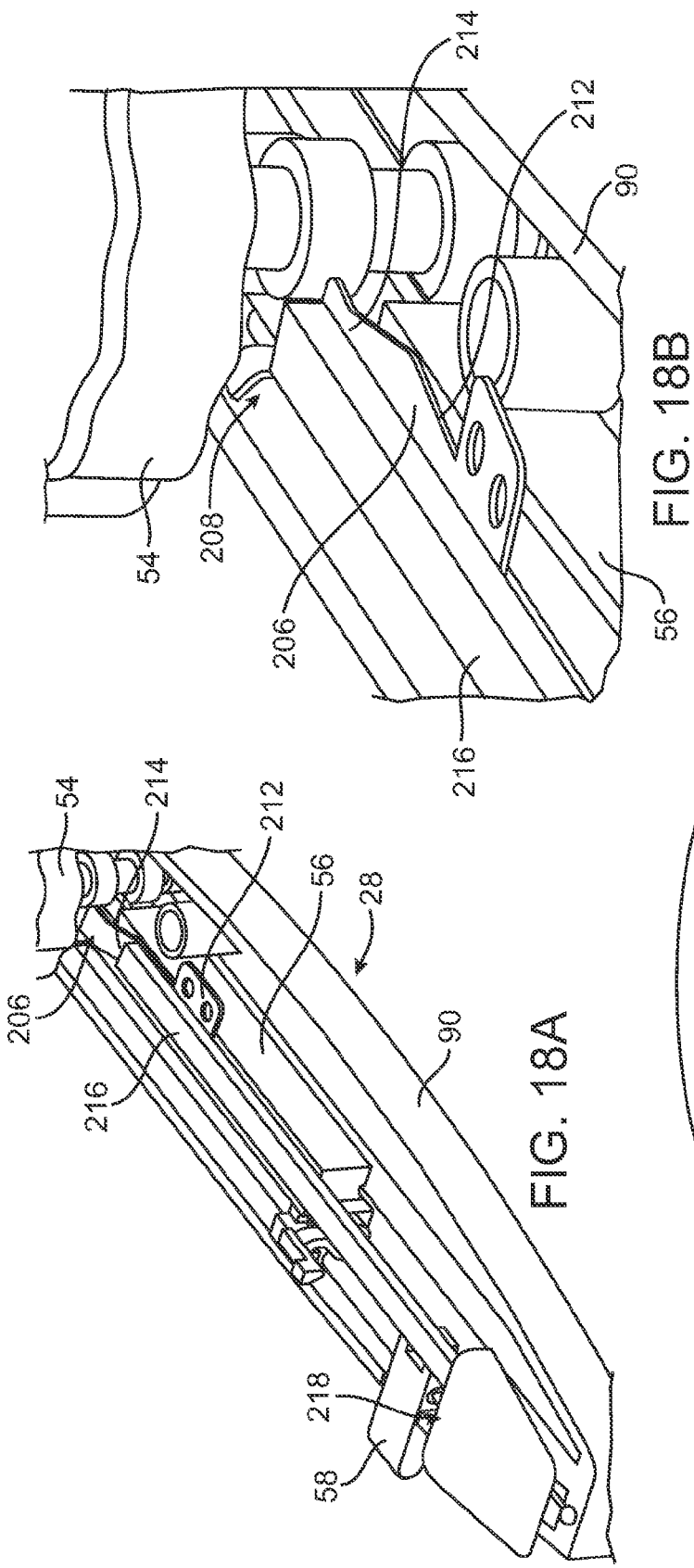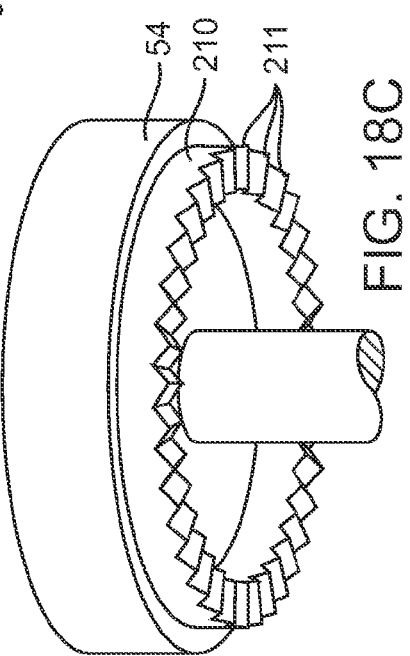

DEVICES AND METHODS FOR CONTROLLING AND INDICATING THE LENGTH OF AN INTERVENTIONAL ELEMENT

CROSS-REFERENCES TO RELATED APPLICATIONS

The present application is a divisional of U.S. application Ser. No. 10/746,466, filed Mar. 30, 2004, the full disclosure of which is incorporated herein by reference.

BACKGROUND OF THE INVENTION

The present invention relates generally to interventional catheters and prostheses, and more specifically to catheters and prostheses for treatment of vascular diseases, including coronary artery disease and peripheral vascular disease, as well as diseases of other body lumens such as the biliary tract, fallopian tubes, urinary and digestive tracts, and other structures.

Balloon angioplasty and stenting are widely used in the treatment of coronary artery disease and peripheral vascular disease. In coronary artery disease, one or more coronary blood vessels become narrowed or closed due to the buildup of stenotic plaques on the arterial wall. This blocks blood flow to the heart muscle, potentially causing myocardial infarction. Such narrowing can also occur in peripheral blood vessels such as the carotids, femorals, iliacs and other arteries, blocking the blood supply to other vital tissues and organs.

Balloon angioplasty involves the use of a long flexible catheter having a balloon at its distal tip. The catheter is inserted into a peripheral artery such as the femoral and advanced transluminally into the diseased artery. The balloon is inflated within the narrowed portion of the vessel, thereby expanding the vascular lumen and restoring normal blood flow.

In some cases, however, balloon angioplasty alone is inadequate to treat vascular disease due to restenosis, the renarrowing of the artery following angioplasty. Stents have been developed to provide an intravascular frame or scaffold to maintain patency of the vascular lumen after it has been expanded. Stents are small tubular prostheses designed to be advanced to the treatment site in a collapsed configuration using an elongated delivery catheter. The stents are then expanded at the treatment site into engagement with the vessel wall to maintain vascular patency.

Stents may be either self-expanding or balloon expandable. Self-expanding stents are made of a shape memory material such as Nitinol and can be delivered in a compressed state within the tip of the delivery catheter and allowed to resiliently expand upon release from the delivery catheter. Balloon expandable stents are made of a malleable metal and are mounted to a balloon on the delivery catheter. When positioned at the treatment site, the balloon is inflated to expand the stent into engagement with the vessel.

Stents, however, have also suffered from the problem of restenosis. Restenosis rates with conventional coronary stents have ranged from 30-40%. The causes of such restenosis are not fully understood. However, it is believed that restenosis may be caused in some cases by the excessive stiffness of current stents and their inability to conform to vascular curves, shapes, dimensional changes, and movements. This problem is particularly acute with longer lesions, which may extend over curved and tapered sections of a vessel and may be subject to non-uniform movements along their lengths.

The need has thus been demonstrated for highly flexible stents that may be used to treat long, curved, and tapered vascular regions. In co-pending U.S. patent application Ser. No. 10/637,713, filed Aug. 8, 2003, entitled "Apparatus and Methods for Delivery of Vascular Prostheses, the full disclosure of which is incorporated herein by reference, highly flexible multi-segmented stents and associated delivery devices are disclosed that enable the treatment of long, curved or tapered vascular lesions. The disclosed delivery devices enable the selective deployment of one or more stent segments at a treatment site to allow the user to customize stent length in situ. Moreover, the device can be repositioned at multiple vascular sites to deploy a plurality of stents of various lengths.

Other custom-length stents and delivery devices are described in co-pending U.S. patent application Ser. No. 10/624,451, filed Jul. 21, 2003, entitled "Apparatus and Methods for Delivery of Multiple Distributed Stents," which is also incorporated herein by reference. This application describes separable stent segments as well as continuous prosthesis structures configured as braids or coils that allow the user to pay out a selected length of the prosthesis structure and deploy it into the vessel at one or more treatment sites.

Variable length angioplasty devices have also been proposed. For example, U.S. Pat. No. 5,246,421 to Saab discloses angioplasty catheters having an elongated balloon and an external sheath that is axially slidable relative to the balloon. The sheath can be retracted to expose a selected length of the balloon for expansion at a treatment site. The catheter can then be repositioned and another length of balloon exposed to treat one or more additional sites.

While such custom-length stents and angioplasty catheters have shown great promise, there remains a need for improved ways of controlling and providing indication of balloon and stent length in such devices. Conventional angioplasty and stenting procedures rely upon the use of fluoroscopy to visualize the location and operation of catheters and prostheses. However, fluoroscopy often fails to provide the clarity, resolution, and precision that are required for the accurate control of stent or balloon length, which in many cases must be controlled within a few millimeters. Moreover, even if visualization were adequate, the user is left to control stent or balloon length by manually manipulating the associated catheters, an operation not well-suited to highly precise control.

BRIEF SUMMARY OF THE INVENTION

The invention provides devices and methods for controlling and indicating the length of an interventional element on a medical device such as a catheter. The devices and methods facilitate accurate control of the working or deployed length of an interventional element by providing highly precise and ergonomic mechanisms for adjusting the length, and by providing indication devices to give the user accurate indications of the length in real time. The types of interventional elements to which the invention may be applied are many, but in preferred embodiments include stents and balloons for the treatment of vascular disease.

In a first aspect of the invention, an interventional catheter comprises an elongated flexible shaft having a distal end and a proximal end, and an interventional element at the distal end, the interventional element having an adjustable length. An actuator is disposed near the proximal end for adjusting the length of the interventional element; and an indication device is disposed near the proximal end for indicating the length to a user. In an exemplary embodiment, the interventional element comprises a balloon. A sheath is movably disposed over the balloon and the actuator is coupled to the sheath to axially reposition the sheath relative to the balloon. In this way the sheath may be used to selectively cover part of the balloon while exposing part of the balloon having a desired length, the sheath constraining the covered part from expansion.

In a further embodiment, the interventional element comprises a stent releasably carried by the shaft. The actuator controls the length of a deployable portion of the stent, the deployable portion being released from the shaft while an undeployed portion of the stent remains associated with the shaft. In one embodiment, the actuator is coupled to a sheath which may be axially positioned to cover a first portion of the stent while a second portion of the stent having a desired length is left uncovered for deployment. The stent may be either balloon expandable or self-expanding. In a preferred embodiment, the stent is comprised of a plurality of separable stent segments and stent length is controlled by exposing a desired number of stent segments outside of the sheath.

In one embodiment, the actuator is movable through a distance correlated with the length. For example, the actuator may be movable through a stroke, each stroke of the actuator adjusting the length a predetermined amount. The actuator may also be configured to allow the length to be adjusted in a first direction and prevent or limit the adjustment of length in a second direction. For example, the actuator may comprise a ratchet mechanism that allows the actuator to move in a first direction to increase the length of the interventional element, but prevents the actuator from moving in the reverse direction to decrease the length.

In some embodiments the indication device is coupled to the actuator. For example, the indication device may comprise a stop that limits the movement of the actuator, thus providing the user a tactile indication of the length. Alternatively, the indication device may comprise a sensor that senses movement of the actuator. Further, the indication device may comprise a visual indicator coupled to the actuator (or to a sensor associated with the actuator) to provide a visual indication of the length of the interventional element based on the actuator position.

The indication device may alternatively comprise a sensor that detects the length of the interventional element. In one embodiment, the sensor may be disposed near the distal end of the shaft and is coupled to an indicator at the proximal end, the indicator being a display or other output device. The sensor may be mechanical, optical, magnetic, inductive, or other suitable type for detecting the length of the interventional element. The output device may provide a visual, audible, tactile, or other signal to the user.

In a further aspect, the indication device comprises a plurality of holes and a movable detent associated with the shaft, each hole being configured to receive the detent, whereby adjusting the length moves the detent from one hole to another hole. As the detent moves from one hole to the next, the reception of the detent in one of the holes provides a tactile indication of the length of the interventional element. In embodiments where a sheath is movably disposed over the shaft to adjust the length of a balloon, stent or other interventional element, the detent or the holes may be disposed on the sheath such that axial movement of the sheath moves the detent from hole to hole.

In a further aspect, the invention provides a stent delivery catheter comprising an elongated flexible shaft having distal and proximal ends and a stent releasably mounted at the distal end, a deployable portion of the stent being releasable from the catheter to assume an expanded configuration, the deployable portion having a length. An actuator is disposed near the proximal end for controlling the length of the deployable portion, and an indication device is disposed on the catheter for indicating the length of the deployable portion to the user.

In some embodiments the actuator is movable through a distance correlated with the length of the portion of the stent to be deployed. For example, the actuator may be movable through a stroke corresponding to a preselected length. This allows the actuator to be actuated repeatedly to adjust the length of the stent to a desired multiple of the preselected length. In exemplary embodiments the stent comprises a plurality of stent segments, and the stroke corresponds to a segment length of one of the stent segments.

The invention contemplates various types of indication devices associated with the catheter. In one embodiment, the indication device comprises a stop that limits the movement of the actuator, thus providing a tactile indication of the length. The actuator or ratchet mechanism may also be configured to emit an audible sound such as a click that indicates the number of strokes or the distance through which the actuator has moved. The indication device may also comprise a plurality of holes or slots and a movable detent, each hole or slot being configured to receive the detent in a manner that can be felt by the user. The indication device may also comprise a sensor for detecting the length of the interventional element. The sensor may be disposed in various locations along the shaft of the interventional device and is usually coupled to an indicator at the proximal end. The sensor may be mechanical, optical, magnetic, inductive, or other suitable type. A display or other output means may be associated with the sensor for providing a visual, audible, tactile, or other indication of the length. The indication device may be configured to indicate a length of the deployable portion of the stent, the number of stent segments in the deployable portion, the number of stent segments (or length of stent) remaining undeployed in the catheter, and other information.

In embodiments in which the stent comprises a plurality of separable stent segments, the actuator may be adapted to axially separate a first stent segment from a second stent segment prior to expansion thereof. This allows the second segment to be expanded and deployed without deploying or interfering with the first segment. In an exemplary embodiment, the actuator has a first position in which it is movable for controlling the number of stent segments in the deployable portion, and a second position in which it is movable for controlling the separation between the first and second stent segments.

The invention further provides methods of using an interventional catheter at a target site in a patient's body. In a first aspect, the method comprises positioning an interventional element of the interventional catheter near the target site with a proximal portion of the interventional catheter being disposed outside the patient's body. A working length of the interventional element is then adjusted with the interventional element remaining positioned in the patient's body. An indication of the working length of the interventional element is received from the proximal portion of the interventional catheter; and, after receiving the indication, the interventional element is deployed.

In exemplary embodiments, the interventional element comprises a balloon, and adjusting the working length comprises constraining a first portion of the balloon from expansion while leaving a second portion of the balloon unconstrained from expansion. Preferably, constraining a first portion of the balloon comprises covering the first portion of the balloon by a sheath movably disposed on the interventional catheter. The indication of the working length then comprises an indication of the length of the second portion.

In some embodiments, the sheath is coupled to an indicator, and the indication of working length being received from the indicator, wherein moving the sheath changes the indication received from the indicator. Receiving the indication of working length may comprise observing a visual indication, hearing an audible indication, feeling a tangible indication, or otherwise receiving a signal from the catheter indicative of the working length. A visual indication may comprise one or more indicia displayed electronically, mechanically, or otherwise on the proximal portion of the interventional catheter. A tactile indication of working length may be received from a detent engaging a hole or other structure associated with the interventional catheter. An audible indication of working length may be received from a clicker or other noise emitter associated with the actuator.

The method may further include, after deploying the interventional element, positioning the interventional element near a second target site; adjusting the working length of the interventional element to a second working length; receiving from the interventional catheter a second indication of the second working length; and after receiving the second indication, re-deploying the interventional element.

In a further aspect of the invention, a method of deploying a stent at a target site in a patient's body comprises positioning a distal end of a delivery catheter near the target site, the stent being releasably coupled to the distal end, a proximal portion of the delivery catheter being disposed outside the patient's body; adjusting the length of a deployable portion of the stent with the delivery catheter positioned in the patient's body; receiving an indication of the length from the proximal portion of the delivery catheter; and after receiving the indication, deploying the deployable portion of the stent at the target site. The indication of working length may be received visually, audibly, tactilely, or in another humanly detectable manner.

Adjusting the length of the deployable portion may comprise moving an actuator associated with the proximal portion of the delivery catheter through a distance correlated with the length. For example the actuator may be movable through a stroke, each stroke of the actuator adjusting the length a predetermined amount. The stent may comprise a plurality of stent segments, and the stroke may then correspond to a segment length of one of the stent segments. The indication device may comprise a stop that limits the movement of the actuator, thus providing tactile indication of length.

The indication of the length may be received from an output device associated with the proximal end of the catheter. The output device may be coupled to a sensor, and the method further comprises detecting the length with the sensor. The sensor may be disposed in any suitable location in the catheter, but in an exemplary embodiment is disposed near the distal end of the delivery catheter in proximity to the stent. The sensor may detect the length mechanically, optically, magnetically, inductively, or in other ways. In other embodiments, the tactile indication is received from a detent engaging a hole associated with the delivery catheter.

In some embodiments, the stent comprises separable stent segments, and adjusting the length comprises constraining at least a first stent segment from expansion while leaving at least a second stent segment unconstrained from expansion. Adjusting the length may comprise moving a sheath relative to the stent segments for selectively covering the first stent segment and exposing the second stent segment. In such embodiments, the indication of length may be correlated with the number of stent segments. Alternatively, the indication of length may be correlated with movement of the sheath relative to the stent.

The method of the invention may further include axially separating the first stent segment from the second stent segment prior to expansion thereof. Such separation may be accomplished using an actuator associated with the proximal portion of the delivery catheter. The actuator may be movable to a first position for controlling the number of stent segments in the deployable portion and further movable to a second position for controlling the separation between the first and second stent segments.

Further aspects of the nature and advantages of the invention will be appreciated from the following detailed description taken in conjunction with the drawings.

BRIEF DESCRIPTION OF THE DRAWINGS

FIG. 1 is a side partial cutaway view of a stent delivery catheter according to the invention with the sheath retracted and expandable member in an expanded configuration.

FIG. 6A is a side cutaway view of the handle of the stent delivery catheter of FIG. 1 with the lever in a down position.

FIG. 6B is a bottom cutaway view of the handle of FIG. 6A.

FIG. 7A is a side cutaway view of the handle of the stent delivery catheter of FIG. 1 with the lever in an up position.

FIG. 7B is a bottom cutaway view of the handle of FIG. 7A.

FIGS. 9A-9B are side elevational views of a further embodiment of the handle of the stent delivery catheter of the invention showing the lever in down and up positions, respectively.

FIGS. 10A-10B and 10C-10D are oblique and transverse cross-sectional views, respectively, of the interior of the handle of FIGS. 9A-9B.

FIG. 15A is a side cutaway view of the handle of the stent delivery catheter of the invention in yet another embodiment thereof.

FIG. 15B is a side elevational view of the handle of FIG. 15A.

FIG. 15C is a bottom cutaway view of the handle of FIG. 15A.

FIG. 18A is a cutaway view of the handle of a stent delivery catheter according to the invention in yet another embodiment thereof.

FIG. 18B is a close-up view of a portion of the handle of FIG. 18A.

FIG. 18C is an oblique view of the actuator knob of the handle of FIG. 18A.

DETAILED DESCRIPTION OF THE INVENTION

Figure 2A:
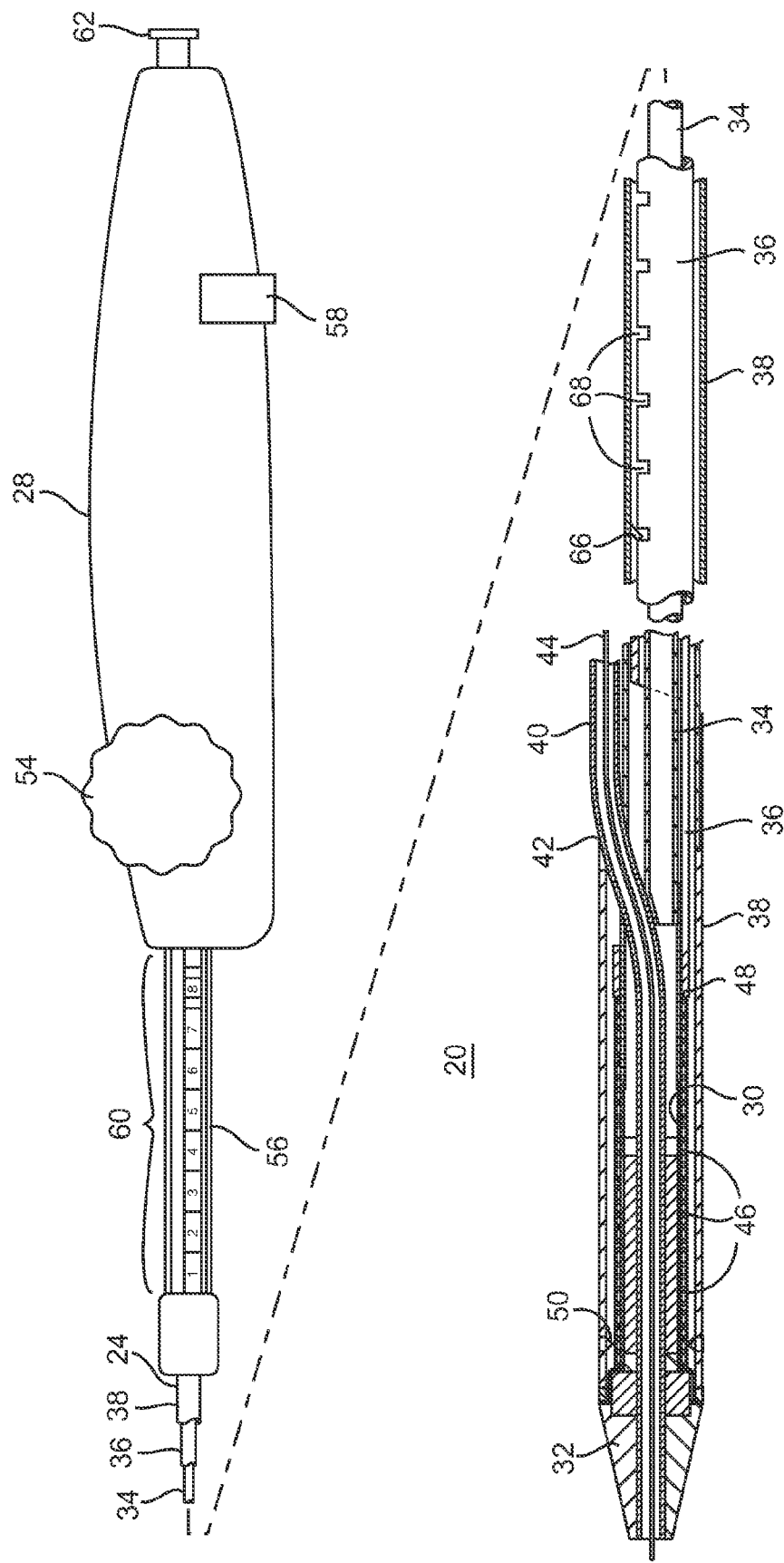
FIGS. 2A-2B are side views of the stent delivery catheter of FIG. 1 with the distal portion in cross-section showing the expandable member in unexpanded and expanded configurations, respectively.

The invention provides devices and methods for manipulation of interventional catheters with greater control, precision, and visibility. In one aspect, the devices and methods of the invention facilitate controlling the working length of an interventional element on a catheter and indicating the working length to the user. In an exemplary embodiment, the interventional element is an expandable member such as a balloon for dilatation of vascular lesions. The interventional element also may comprise a stent or series of stent segments. However, the principles of the invention will have applicability to various types of interventional elements for use in various parts of the body, wherever highly precise catheter manipulation and control and visibility of working length may be desirable.

Referring to FIG. 1, in a first embodiment of the invention, a stent delivery catheter 20 comprises an elongate flexible shaft 22 having a proximal end 24 and a distal end 26. Shaft 22 is comprised of a plurality of coaxial members including an inflation shaft 34, a pusher 36, and a sheath 38. A handle 28 is mounted to sheath 38 at proximal end 24. Near distal end 26, expandable member 30, shown in an expanded configuration, is mounted at its proximal end to inflation shaft 34. A guidewire tube 40 extends through a port 42 in sheath 38 and extends through the interior of expandable member 30 to distal end 26. Expandable member 30 is attached at its distal end to guidewire tube 40, and a nosecone 32 is mounted to guidewire tube 40 distally of expandable member 30. A guidewire 44 is slidably positionable through guidewire tube 40 and nosecone 32 to facilitate guidance of catheter 20 through the vasculature.

A plurality of stent segments 46 are slidably positioned over expandable member 30. Pusher 36 is axially slidable relative to inflation shaft 34 and engages stent segments 46 at its distal end 48. Pusher 36 may be pushed distally to advance stent segments 46 over expandable member 30, or pusher 36 may be held in a stationary position while expandable member 30 is drawn proximally relative to stent segments 46. Sheath 38 is axially movable relative to expandable member 30, pusher 36, and stent segments 46. Sheath 38 may be repositioned proximally or distally to selectively expose a desired length of the expandable member and stent segments thereon according to the length of the lesion to be treated. Sheath 38 and pusher 36 may be drawn proximally in tandem relative to expandable member 30 to separate stent segments 46 exposed distally of sheath 38 from stent segments 46 held within sheath 38. Various other aspects of the construction of delivery catheter 20 and stent segments 46 are described in copending application Ser. No. 10/637,713, filed Aug. 8, 2003, which has been incorporated herein by reference.

A stent valve 50 is mounted to the interior of sheath 38 and is preferably spaced proximally from the distal end 52 of sheath 38 a distance equal to the length of about ½-1 stent segment. Stent valve 50 comprises an annular ridge configured to frictionally engage stent segments 46 to facilitate control of the spacing between those segments to be deployed distally of sheath 38 and those to be retained within sheath 38. Stent valve 50 may also comprise any of the structures described in copending application Ser. No. 10/412,714, filed Apr. 10, 2003, which is incorporated herein by reference.

Handle 28 includes an actuator knob 54 rotatably coupled thereto. A post 56 is mounted to handle 28 so as to be extendable distally out of the handle and retractable proximally into the handle. Sheath 39 is attached to post 56. Rotation of actuator knob 54 extends or retracts post 56, thereby moving sheath 38 relative to expandable member 30. A lever 58 is pivotably coupled to handle 28 and is movable between a first position in which rotation of actuator knob 54 moves only sheath 38, and a second position in which rotation of actuator knob 54 moves both sheath 38 and pusher 36 relative to expandable member 30, as described more fully below.

A plurality of indicia 60 are disposed on post 56. Indicia 60 comprise alphanumeric symbols or other appropriate indicators of the length of expandable member exposed distally of sheath 38 and/or the number or length of stent segments 46 exposed for deployment. As described more fully below, a pointer or other reference object may be used that points to the appropriate location among indicia 60 corresponding to the number or length of stent segments 46 that have been exposed; preferably such pointer is adapted to compensate for retraction of sheath 38 in tandem with pusher 36, during which additional stent segments are not exposed distally of sheath 38, as described more fully below.

A luer fitting 62 is mounted to a proximal end of handle 28 and is in fluid communication with an inflation lumen (not shown in FIG. 1) in inflation shaft 34. Luer fitting 62 is adapted for coupling to an inflation device to enable delivery of inflation fluid into expandable member 30, for example, an Indeflator™ inflation device available from Guidant Corp. of Santa Clara, Calif.

Figure 2B:
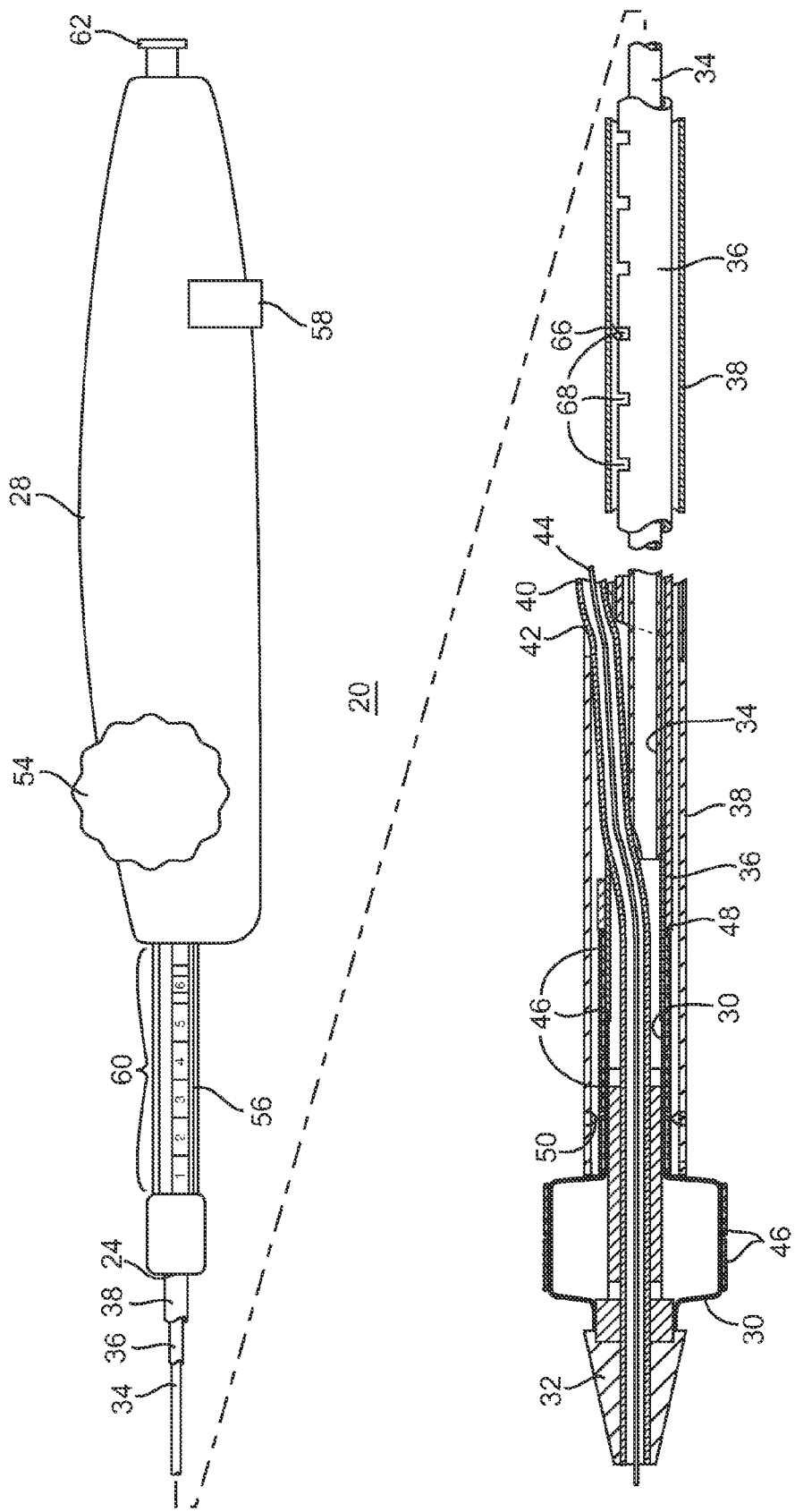

Referring to FIGS. 2A-2B, delivery catheter 20 includes a device for providing a tactile indication of the number of stent segments 46 exposed from sheath 38 in addition to the visual indication provided by indicia 60. In this embodiment, the indication device consists of a detent 66 extending inwardly from the inner wall of sheath 38, and a series of slots 68 arranged axially at spaced-apart locations on pusher 36. Detent 66 and slots 68 may be located in a distal portion of delivery catheter 20 just proximal to expandable member 30, in a middle portion of the catheter proximal to guidewire port 42, or near the proximal end 24 distally of or within post 56 or handle 28. Detent 66 is preferably a cantilevered extension integrally formed with sheath 38, being cut, for example, out of the wall of sheath 38, and is resiliently deflectable and biased toward pusher 36. Detent 66 may alternatively be a bump or ridge on the inner wall of sheath 38 configured to engage slots 68. Slots 68 may be holes, apertures, depressions, recesses, ridges, bumps or any other suitable structure for receiving or catching on detent 66. The spacing of slots 68 is selected to provide an indication of the distance that sheath 38 is translated relative to pusher 36. In a preferred embodiment, the spacing is equal to the length of 1 stent segment 46, although ½, twice, or other known fraction or multiple of the length of a stent segment 46 are also possible. As sheath 38 is retracted proximally relative to pusher 36, detent 66 catches in each slot, providing a tactile "bump" that can be felt through handle 28. In this way, as knob 54 is turned to retract sheath 38, the user knows that each bump corresponds to the length of one stent segment, meaning that one stent segment has been exposed distally of sheath 38 with each bump. By feeling such bumps and by observing indicia 60, the user can precisely retract the sheath to expose the number of stent segments needed to match the length of the lesion being treated, as illustrated in FIG. 2B.

Figure 3:
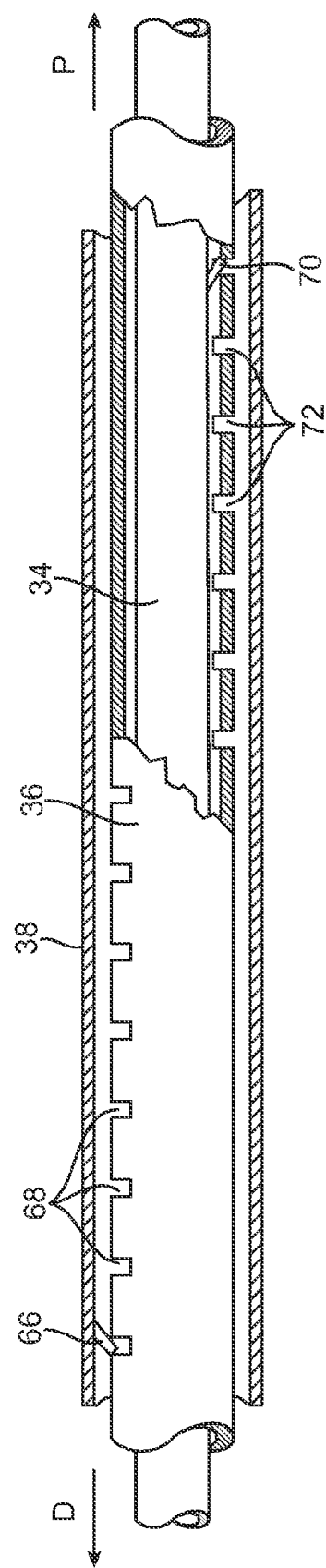
FIG. 3 is a side cross-sectional view of a portion of the shaft of the stent delivery catheter of the invention in a further embodiment thereof.

In a further embodiment, illustrated in FIG. 3, delivery catheter 20 further includes a device for providing a tactile indication of the distance that both sheath 38 and pusher 36 are retracted in tandem relative to expandable member 30. In this embodiment, a second detent 70 is disposed on the outer wall of inflation shaft 34 and extends outwardly to engage a series of axially spaced slots 72 in pusher 36. Detent 70 and slots 72 may be constructed similarly to detent 66 and slots 68 described above, and may be located in a distal, middle, or proximal portion of delivery catheter 20. The spacing of slots 72 is selected to provide the user with an indication of the distance that pusher 36 is retracted relative to the expandable member 30. For example, after sheath 38 has been retracted relative to pusher 36 and expandable member 30 so as to expose a desired number of stent segments, the user may wish to create separation between the stent segments 46 exposed distally of sheath 38 and those stent segments 46 remaining within sheath 38. This is accomplished by retracting both sheath 38 and pusher 36 in tandem, wherein detent 66 is stationary relative to slots 68. As sheath 38 and pusher 36 are retracted, detent 70 moves from one slot 72 to another, providing a tactile "bump" that can be felt through handle 28. The currently preferred separation distance is about ½-1 times the length of one stent segment 46. Thus, with slots 72 spaced apart a distance of ½ stent segment, after exposing the desired number of stent segments, the user can retract pusher 36 and sheath 38 one or two "bumps" to create the desired separation.

Figure 4A:
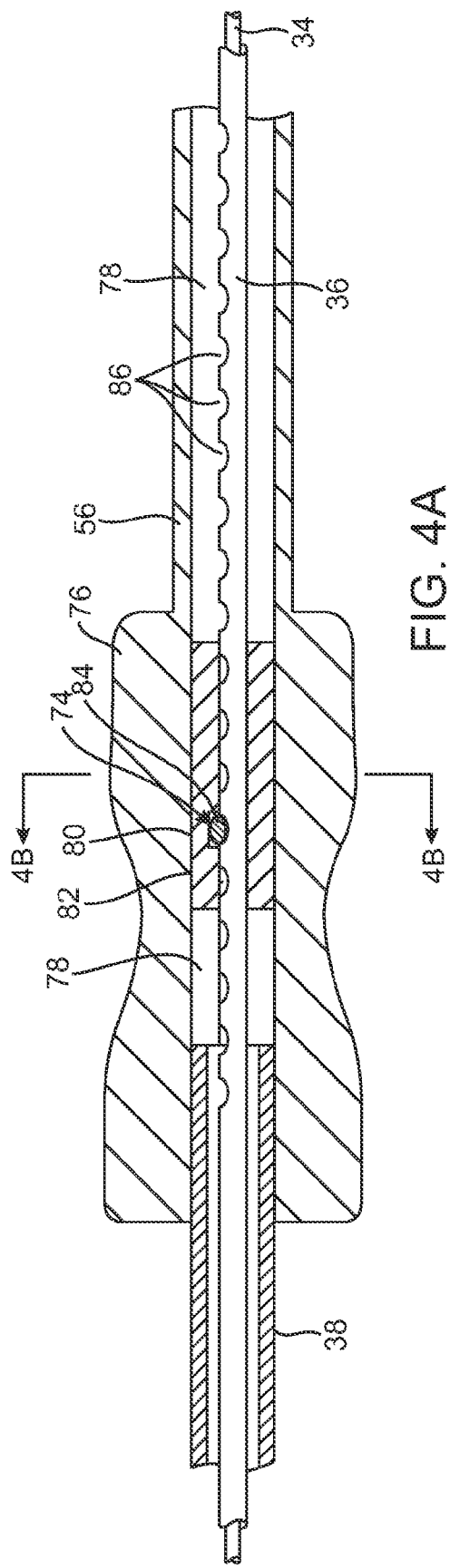
FIG. 4A is a side cross section of a distal portion of the post in the handle of the stent delivery catheter of the invention in another embodiment thereof.
Figure 4B:
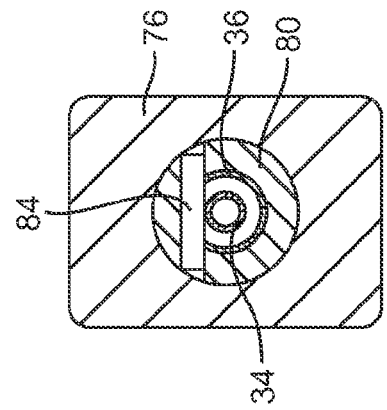
FIG. 4B is a transverse cross section of the post of FIG. 4A.
Figure 5A:
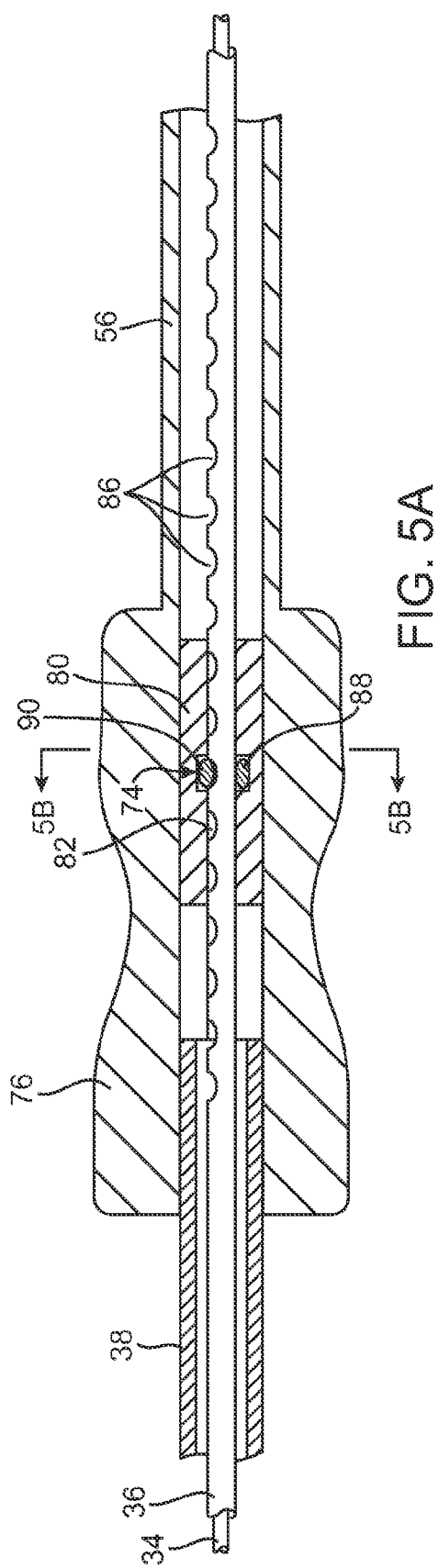
FIG. 5A is a side cross section of the post of the handle of the stent delivery catheter of the invention in a further embodiment thereof.
Figure 5B:
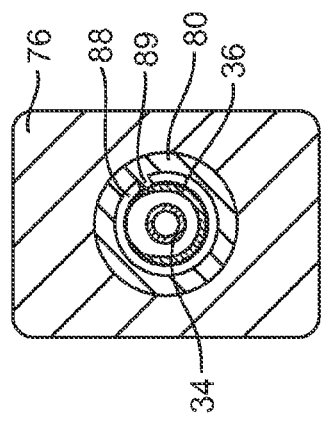
FIG. 5B is a transverse cross section of the post of FIG. 5A.
Figure 5C:
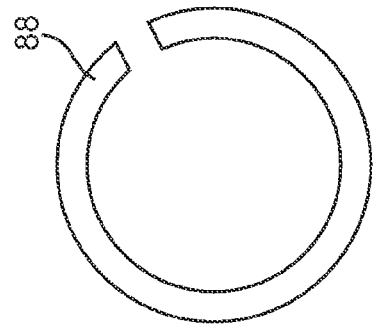
FIG. 5C is a top elevational view of a clip within the post of FIG. 5A.

FIGS. 4A-4B and 5A-5C illustrate alternative embodiments of a detent for providing a tactile indication of the degree of sheath retraction to the user. In FIGS. 4A-4B, a detent 74 is located within a block 76 at the distal end of post 56 on handle 28. An axial passage 78 extends through post 56 and block 76. At the distal end of axial passage 78, sheath 38 is fixed to block 76 by adhesive, set screw, or other suitable means of attachment. Pusher 36 extends slidably through passage 78. A bullet 80 is fixed within passage 78 and has an interior lumen 82 of sufficient size that pusher 36 is slidable therein. A detent pin 84 is disposed transversely through bullet 80 and cuts through lumen 82 along an upper edge thereof, as seen in FIG. 4B. Pusher 36 has a series of transverse slots 86 in axially-spaced locations aligned with detent pin 84. In this way, as sheath 38 is retracted relative to pusher 36, detent pin 84 engages and seats in each slot 86, allowing the user to feel a bump as each slot is engaged.

In the embodiment of FIGS. 5A-5C, detent 74 is again located within block 76 at the distal end of post 56. In this embodiment, however, detent 74 comprises a C-shaped clip 88 disposed within an annular channel 89 in bullet 80. C-shaped clip 88 is a fairly hard, resilient material such as nickel titanium alloy or other suitable metal or polymer. C-shaped clip 88 is positioned so as to cut through lumen 82 along an upper edge thereof in alignment with slots 86 on pusher 36. Again, as sheath 38 is retracted relative to pusher 36 C-shaped clip 88 engages and seats within each slot 86, providing tactile feedback to the user as to the degree of sheath retraction and number of stent segments 46 exposed distally thereof for deployment.

FIGS. 6A-B and 7A-B illustrate the interior of handle 28 with lever 58 in "down" and "up" positions, respectively. Handle 28 has a housing 90 having an ergonomic shape designed for gripping in one hand. Actuator knob 54 is rotatably coupled to housing 90 in a location suitable for engagement with the user's thumb or forefinger. Post 56 extends slidably through the distal end of housing 90 and has a rack 92 disposed on an upper surface thereof. A pinion gear 96 is mounted to actuator knob 54 for rotation therewith. Pinion gear 96 engages rack 92 such that rotation of actuator knob 54 translates post 56, along with sheath 38 mounted thereto, distally or proximally relative to handle 28.

Pusher 36 extends slidably through post 56 as described above and is fixed at its proximal end to a puck 98. Puck 98 is pivotably coupled to a brake 100, which is slidably mounted to a rail 102. Rail 102 is coupled to lever 58 at its proximal end and to a hinge 104 at its distal end such that movement of lever 58 from the down position of FIGS. 6A-B to the up position of FIGS. 7A-B rotates rail 102 along with brake 100 about an axis A. Springs 106 at each end of rail 102 bias lever 58 toward the up and down positions.

Brake 100 has a plurality of teeth 108, 110 along opposing lateral edges thereof, as seen in FIG. 6B. A brake rack 112 is mounted to the inner surface of housing 90 and has a series of teeth configured to engage teeth 108 of brake 100. When lever 58 is in the down position of FIGS. 6A-B, teeth 108 engage brake rack 112, thus holding pusher 36 in a stationary position relative to handle 28. In this way, as knob 54 is rotated, sheath 38 is retracted relative to both pusher 36 and inflation shaft 34 to expose stent segments 46 on expandable member 30 distally of sheath 38.

Referring to FIGS. 7A-B, a coupling rack 114 is disposed on a lower surface of post 48 and has a plurality of teeth configured to engage teeth 110 on brake 100. With lever 58 in the up position, teeth 108 on brake 100 are disengaged from brake rack 112 and teeth 110 (not visible in FIGS. 7A-B) are engaged with coupling rack 114. This allows pusher 36 to move in tandem with post 56 and sheath 38. In this manner, rotation of actuator knob 54 retracts both sheath 38 and pusher 36 relative to inflation shaft 34, allowing separation to be created between stent segments 46 exposed distally of sheath 38 and those stent segments 38 retained within sheath 38.

Figure 8A:
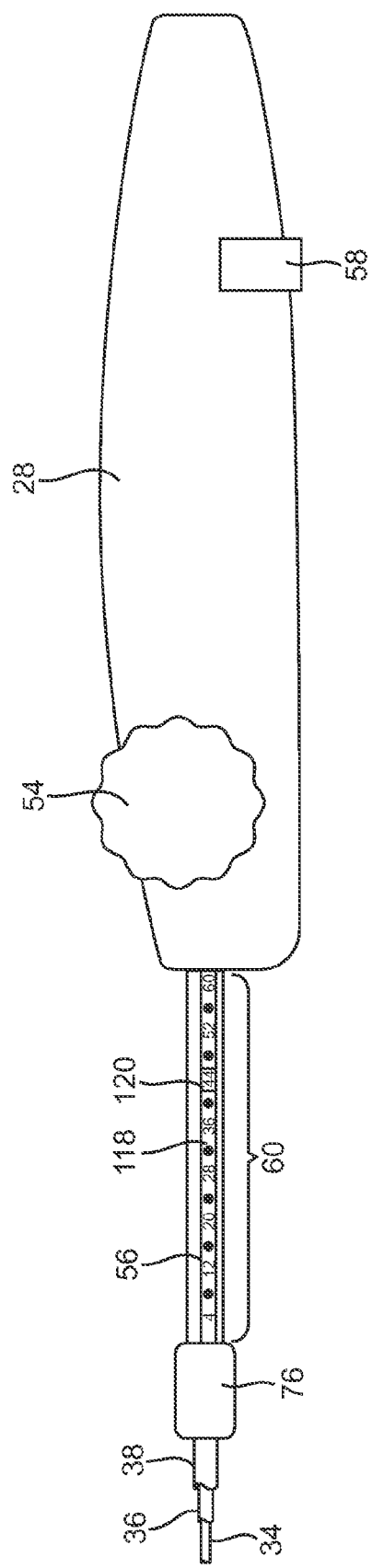
FIGS. 8A-8B are side elevational views of the handle of the stent delivery catheter of FIG. 1 showing the sheath in unretracted and retracted positions, respectively.
Figure 8B:
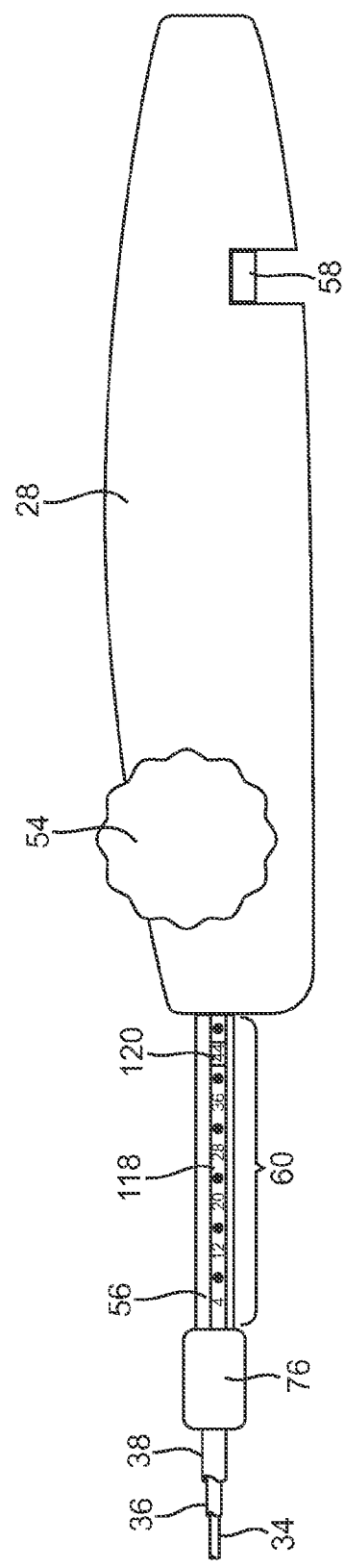

Referring now to FIGS. 8A-8B, visual indication devices for indicating the extent of sheath retraction or the number of stent segments exposed from sheath 38 will be described. In a preferred embodiment, post 56 has an axial slot or window 118 disposed lengthwise thereon. Indicia 60 are applied to post 56 adjacent to window 118 or on a translucent cover over window 118. An indicator 120 of contrasting color is mounted to pusher 36 within post 56 in alignment with window 118. In this way, as post 56 is retracted relative to pusher 36, indicia 60 move relative to indicator 120. In a preferred embodiment, indicia 60 comprise numbers corresponding to the number of stent segments 46 carried by delivery catheter 20. The indicator 120 may be configured to point to the number of stent segments 46 exposed for deployment as sheath 38 is retracted. Alternatively, indicator 120 may be configured to point to the number of stent segments 46 remaining within sheath 38. It should further be noted that when lever 58 is moved to the up position of FIG. 8B, wherein sheath 38 and pusher 36 move in tandem, indicator 120 remains stationary relative to indicia 60 so that the process of creating separation between stent segments 46 does not alter the indication of the number of stent segments being deployed.

Figure 8C:
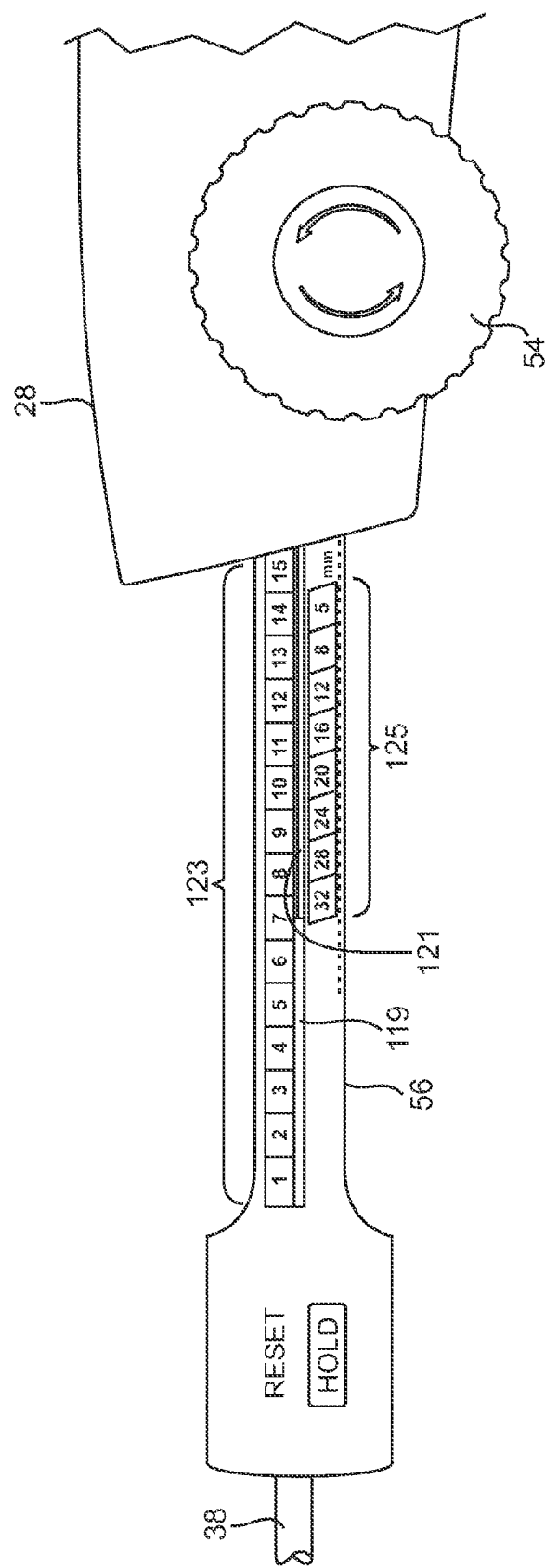
FIG. 8C is a side elevational view of a further embodiment of a handle in the stent delivery catheter of the invention.
Figure 10B:
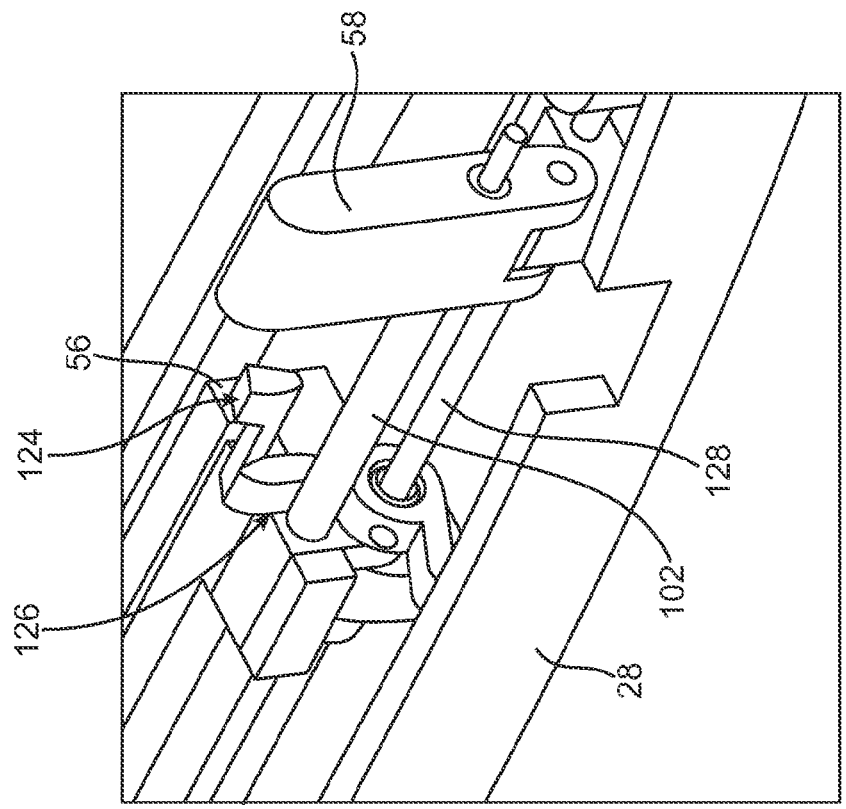
Figure 10A:
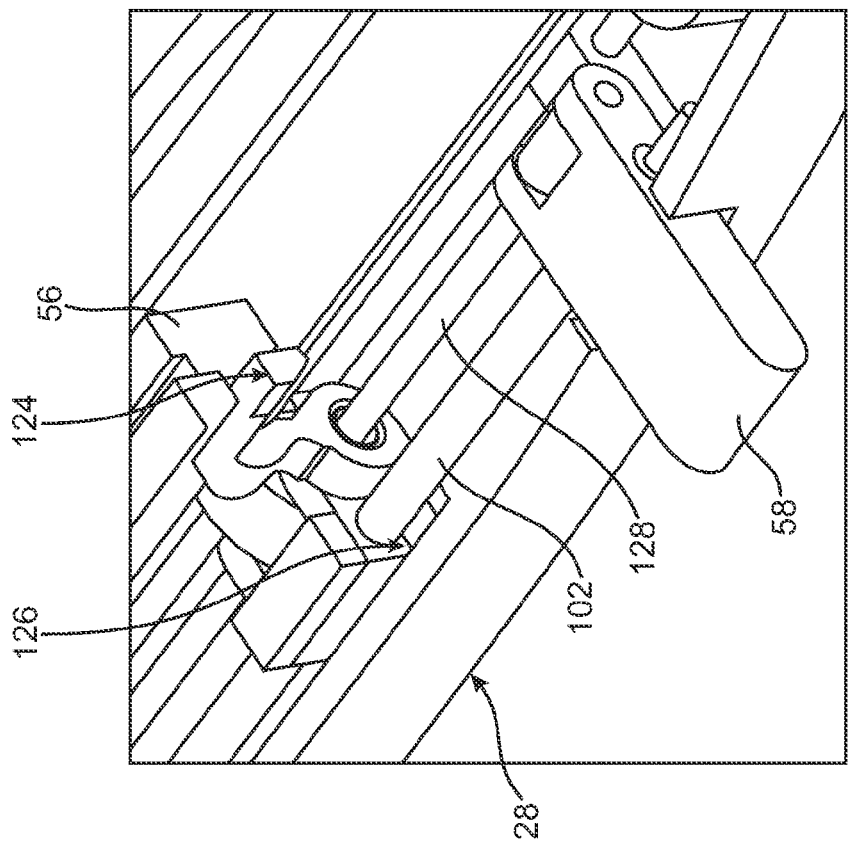

FIG. 8C illustrates another embodiment of visual indicators on post 56. As in the embodiment of FIGS. 8A-B, an axial slot 119 is disposed in post 56 to expose an indicator bar 121, which is fixed to pusher 36 and is movable relative to post 56. A first series of indicia 123 are disposed on post 56 adjacent slot 119. As stent segments 46 are exposed and deployed, indicator bar 121 moves relative to first indicia 123 to indicate the number of stent segments 46 remaining within sheath 38. A second set of indicia 125 are disposed on post 56 on the opposite side of slot 119 from first indicia 123 and move with post 56 relative to a reference point fixed relative to handle 28. In an exemplary embodiment, the reference point is the distal edge 127 of handle 28. As sheath 38 is retracted, second indicia 125 indicate the length or number of stent segments 46 being exposed distally of sheath 38.

In an alternative embodiment, illustrated in FIGS. 9A-B, a window 122 is disposed in handle 28, with indicia 60 applied adjacent to window 122 or to a translucent cover thereon. An indicator 124 is mounted to post 56 within handle 28 and is visible through window 122 when lever 58 is in the down position of FIG. 9A. Retraction of post 56 thus moves indicator 124 relative to indicia 60. Following sheath retraction, when separation is to be created between stent segments 46, lever 58 is moved to an up position as in FIG. 9B and indicator 124 is no longer visible through window 122. As shown in FIGS. 10A-10D, indicator 124 is mounted to an angled arm 126 pivotably coupled to an axle 128 aligned with the axis of rotation of lever 58. As lever 58 is pivoted to its up position as in FIGS. 10B and 10D, rail 102 engages arm 126 and pivots indicator 124 laterally, thereby displacing it from window 122. When lever 58 is returned to the down position as in FIGS. 10A and 10C, rail 102 again engages arm 126 and returns indicator 124 to a position in which it is visible through window 122.

Figure 11B:
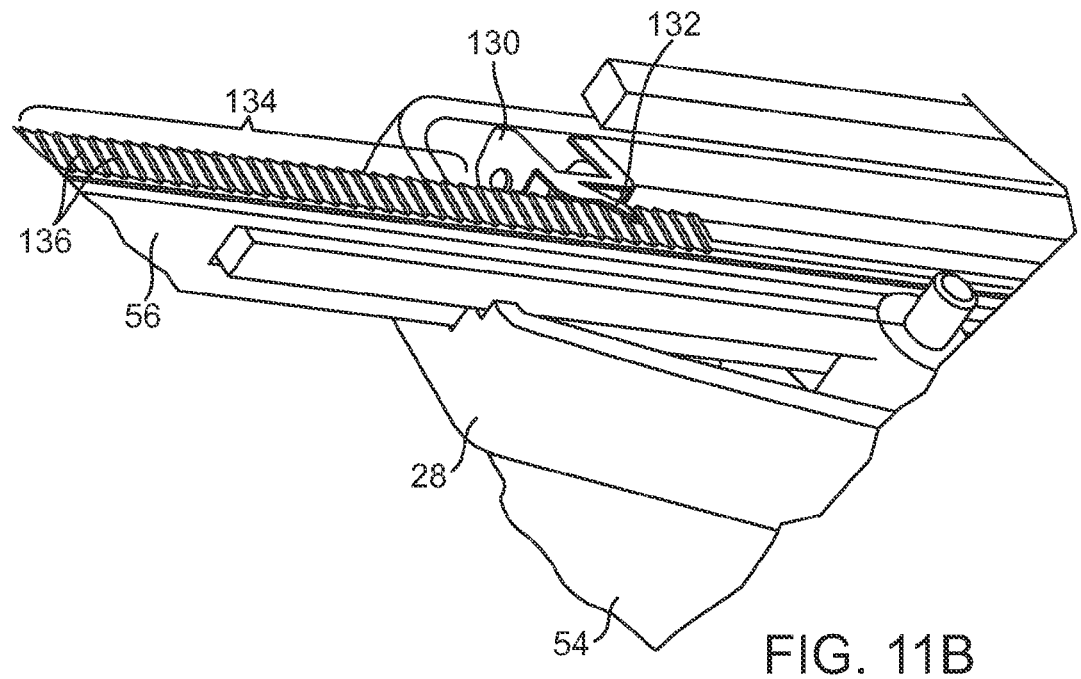
FIGS. 11A-11B are oblique views of the interior of a further embodiment of a handle in the stent delivery catheter of the invention.
Figure 11A:
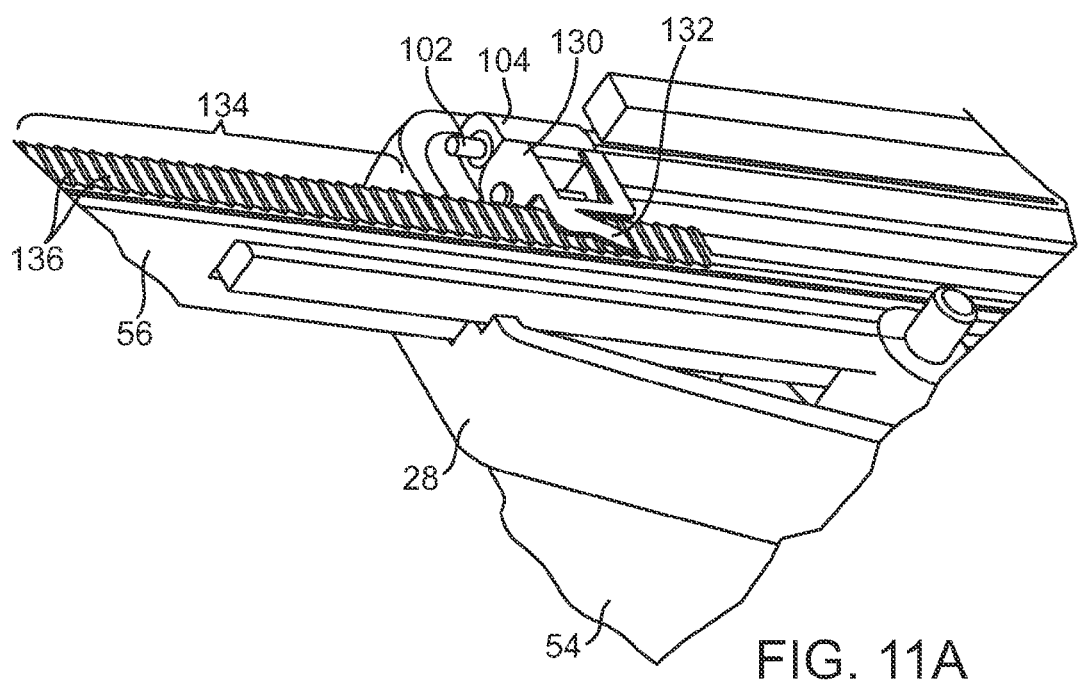

In a further embodiment, stent delivery catheter 20 includes a ratchet mechanism serving to provide an audible and/or tangible indication of sheath retraction, as well as to limit travel of the sheath to a single direction (e.g. proximal). Preferably the ratchet may be selectively enabled, so that the ratchet is engaged when sheath 38 is retracted relative to pusher 36, but is disengaged when sheath 38 and pusher 36 are retracted together relative to expandable member 30. In an exemplary embodiment, illustrated in FIGS. 11A-11B, a ratchet frame 130 is mounted to hinge 104, which, as described above with reference to FIG. 6-7, is coupled to rail 102 and pivots therewith when lever 58 is actuated. Ratchet frame 130 has a pawl 132 configured to engage a rack 134 on post 56. Rack 134 has a series of stepped teeth 136 oriented so as to be slidable proximally relative to pawl 132, but in the distal direction pawl 132 engages the vertical trailing edges of teeth 136 to stop distal movement. Pawl 132 is flexible and resilient so as to ride up over each tooth and spring back at the vertical trailing edge, making an audible and tangible "click." When lever 58 is in the down position of FIGS. 6A-6B so as to lock pusher 36 relative to handle 28, hinge 104 is disposed in the position shown in FIG. 11A, urging pawl 132 into engagement with rack 134. This limits sheath movement to the proximal direction and causes pawl 132 to create an audible and tangible indication of sheath retraction. When lever 58 is flipped to the "up" position of FIGS. 7A-7B wherein pusher 36 becomes fixed relative to sheath 38, ratchet frame 130 pivots with hinge 104 away from post 56, disengaging pawl 132 from rack 134, as shown in FIG. 11B. This allows the user to adjust the separation distance of exposed stents segments relative to unexposed stent segments without restriction on the movement of sheath 38 and pusher 36. It will be understood that the ratchet mechanism described above is only exemplary and mechanisms of various types and at various locations in stent delivery catheter 20 are possible. For example, a circular rack of stepped teeth could be coupled to knob 54, and a pawl could be mounted within handle 28 so as to engage the rack as knob 54 is rotated, as described more fully below.

Figure 12A:
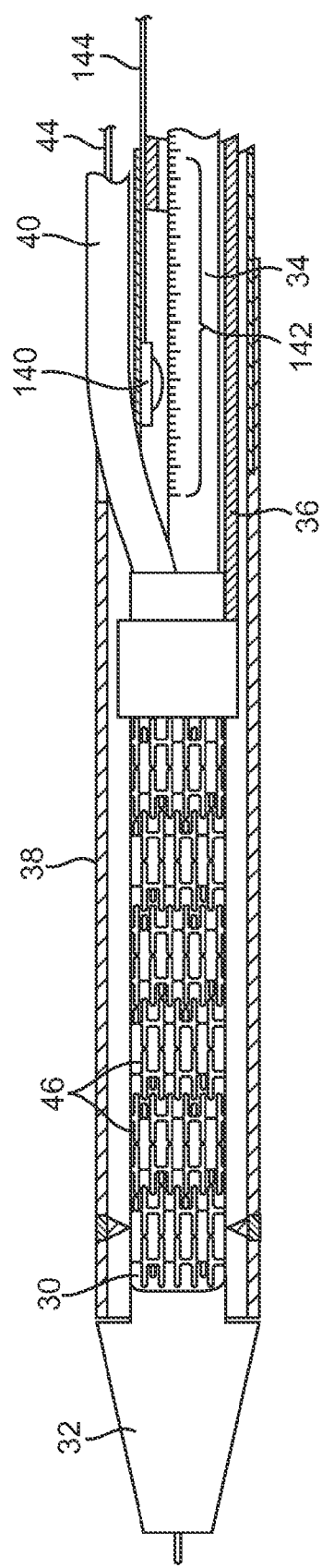
FIGS. 12A-12B, 13, and 14 are side cross-sectional views of a distal portion of a stent delivery catheter according to the invention in a further embodiment thereof showing alternative sensory devices.

The interventional catheters of the invention may further include sensory devices for detecting the relative positions of catheter components, the length of balloon or stent exposed for deployment, the number of stent segments exposed, and other parameters. In a first embodiment illustrated in FIG. 12A, a sensor 140 is mounted to the inner wall of sheath 138 and is adapted to detect its position relative to inflation shaft 34 and/or pusher 36. Sensor 140 may be any of various types, but in one embodiment comprises an optical encoder capable of detecting a series of marks or lines 142 disposed on the outer surface of inflation shaft 34 (alternatively such marks could be placed on the outside of pusher 36). Sensor 140 includes a wire 144 extending proximally through sheath 38 into handle 28, where it may be coupled to an appropriate power supply and output device for displaying the detected position. Alternatively sensor 140 may be wireless and may transmit signals via radio waves, infrared signals, or other suitable manner. Various types of suitable optical encoders are available, including those described in U.S. Pat. No. 5,965,879, which is incorporated herein by reference. Alternatively, sensor 140 could be a magnetic or inductive sensor and a series of ferromagnetic stripes or bands could be applied to pusher 36 in place of marks 142.

Figure 12B:
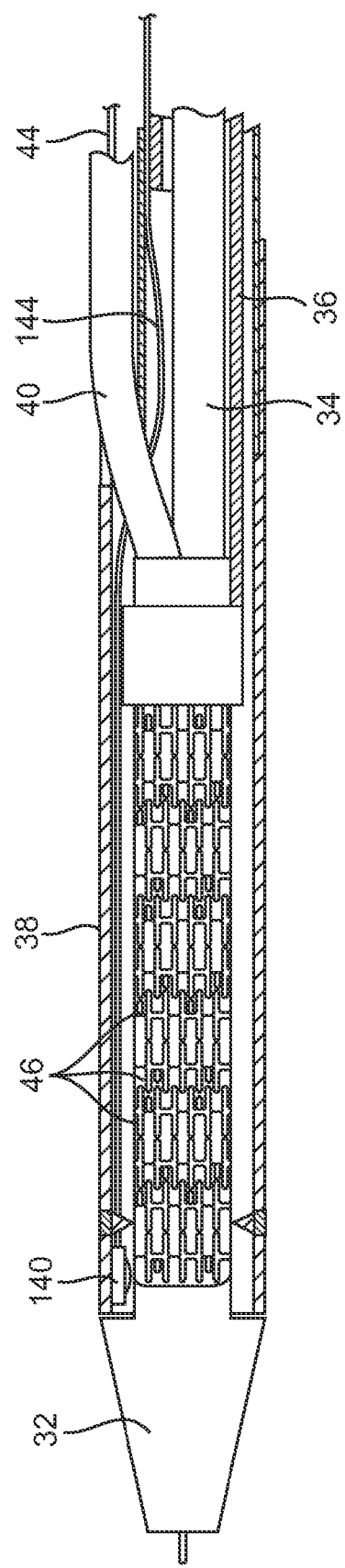

It should be noted that sensor 140 may be placed in virtually any location along the extremity of delivery catheter 20 from handle 28 to expandable member 30. Preferably, however, sensor 140 is located near the distal end of delivery catheter 20. This has the advantage of providing a precise indication of the actual displacement of sheath 38 near the distal end, without distortion as a result of the stretching or compression of sheath 38, pusher 36, or inflation shaft 34. In another configuration, illustrated in FIG. 12B, sensor 140 is mounted near the distal end 52 of sheath 38. Sensor 140 is adapted for detecting each stent segment 46 or each strut within stent segments 46 as sheath 38 is retracted past each segment. For example, sensor 140 may be an optical encoder capable of detecting and counting the struts of each stent segment or suitable markings on each stent segment. As another alternative, a series of opaque or reflective marks may be applied to expandable member 30, stent segments 46, or guidewire tube 40 that can be optically detected by sensor 140 as sheath 38 is retracted.

Figure 13:
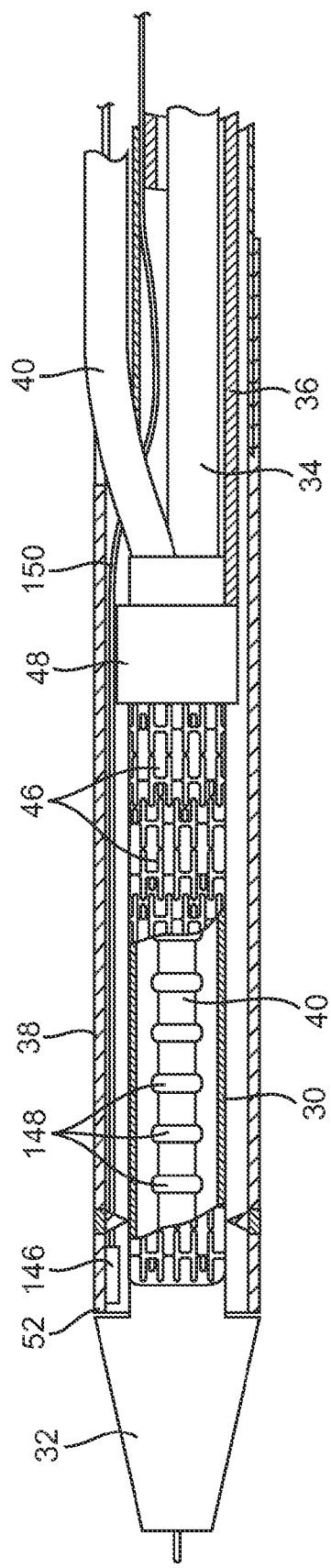

In a further embodiment, illustrated in FIG. 13, a sensor 146 is mounted to the inner wall of sheath 38 near its distal end 52. Sensor 146 may be any of a variety of types suitable for sensing the displacement of sheath 38 relative to stent segments 46, expandable member 30, or guidewire tube 40. For example, sensor 146 may be a magnetic sensor, and a plurality of magnetic bands 148 may be mounted to guidewire tube 40 within expandable member 30. As sheath 38 is retracted relative to guidewire tube 40, sensor 146 detects each magnetic band 148, which may be spaced apart a known distance such as the length of one stent segment 46. A wire 150 extends from sensor 146 proximally through sheath 38 to handle 28, where it is coupled to a suitable power supply, processor, and output display (or sensor 146 could be wireless). The output display (or audible output device) may display the number of stent segments, the length of stent segments, or the length of expandable member 30 that has been exposed distally of sheath 38.

Figure 14:
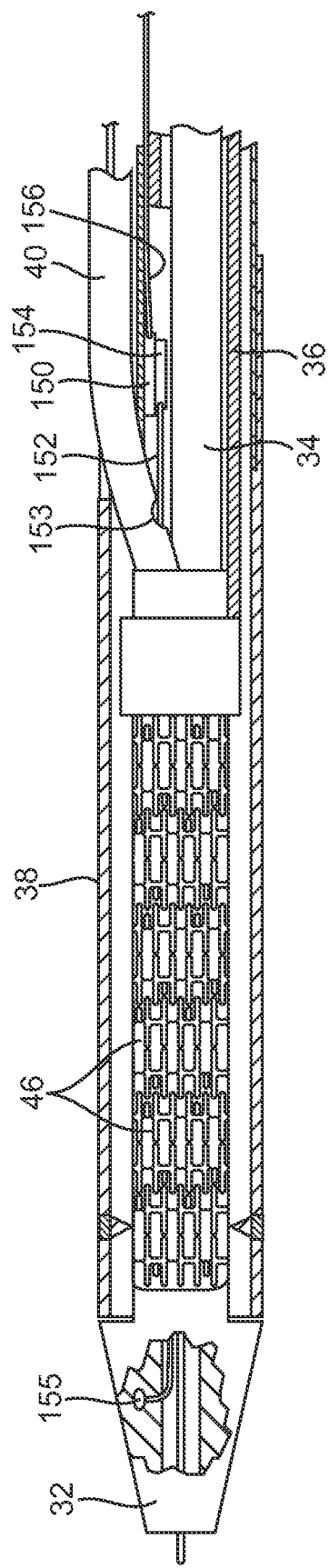

In another embodiment, illustrated in FIG. 14, a displacement sensor 150 is mounted to sheath 38 just proximal to port 42 through which guidewire tube 40 extends. Displacement sensor 150 may be a draw-wire displacement sensor (or so-called "electronic tape measure") that has an extendable wire 152 biased to retract into a housing 154 (see for example, www.micro-epsilon.com). Wire 152 extends through a hole 153 in guidewire tube 40 and passes slidably through guidewire tube 40 into nosecone 32. Wire 152 has an anchor 155 at its distal end that is fixed to nosecone 32. As sheath 38 is retracted, wire 152 is extended from housing 154. An encoder within housing 154 (not shown) detects the length of wire that has been drawn out (or the number of rotations of a spool around which the wire is wound). A conductor wire 156 extends proximally into handle 28 and is coupled to an appropriate power supply, processor, and output display. The exact displacement of sheath 38 relative to nosecone 32 (and expandable member 30) is thus detected and indicated to the user. Of course, displacement sensor 150 may be mounted at any suitable location along stent delivery catheter 20, including within handle 28, and may be adapted to detect the displacement of any of the various movable components including sheath 38, pusher 36, inflation shaft 34, or stent segments 46.

FIGS. 15A-15C illustrate still another embodiment of a stent delivery catheter according to the invention. In this embodiment, handle 28 is constructed in the manner described above except in place of actuator knob 54, a motor 160 is mounted to housing 90. Motor 160 may be a stepper, servo, or other suitable motor of appropriate size and delivering the necessary level of torque, speed, and power. A drive shaft 162 of motor 160 is coupled to pinion gear 96. Motor 160 is coupled to a switch 164 and a power supply such as a battery (not shown). In addition, motor 160 includes an encoder (not shown) that detects the degree of rotation of drive shaft 162. The encoder may be coupled to a processor 166 and an output display 168 that is visible through handle housing 90. In this way, motor 160 may be actuated using switch 164 to rotate pinion gear 96 and thereby retract post 56 and sheath 38. The user can view the amount of retraction (by either number of stent segments or their length) on display 168. Preferably switch 164 may be actuated in two directions so as to move motor 160 either forward or backward, thus allowing precise control of the position of sheath 38.

In a preferred embodiment, switch 164 is adapted to enable the user to select the desired amount of sheath retraction, whereupon motor 160 will automatically retract sheath 38 the appropriate amount. For example, switch 164 could be pressed once to retract the sheath the length of one stent segment, twice for two stent segments, etc. Alternatively, a dial or sliding switch could be used so that various switch positions or the degree of switch displacement corresponded to the desired amount of retraction. In these embodiments, motor 160 could include a feedback loop from its encoder so that motor 160 automatically rotated drive shaft 162 the amount needed to achieve the desired degree of sheath retraction.

Figure 16:
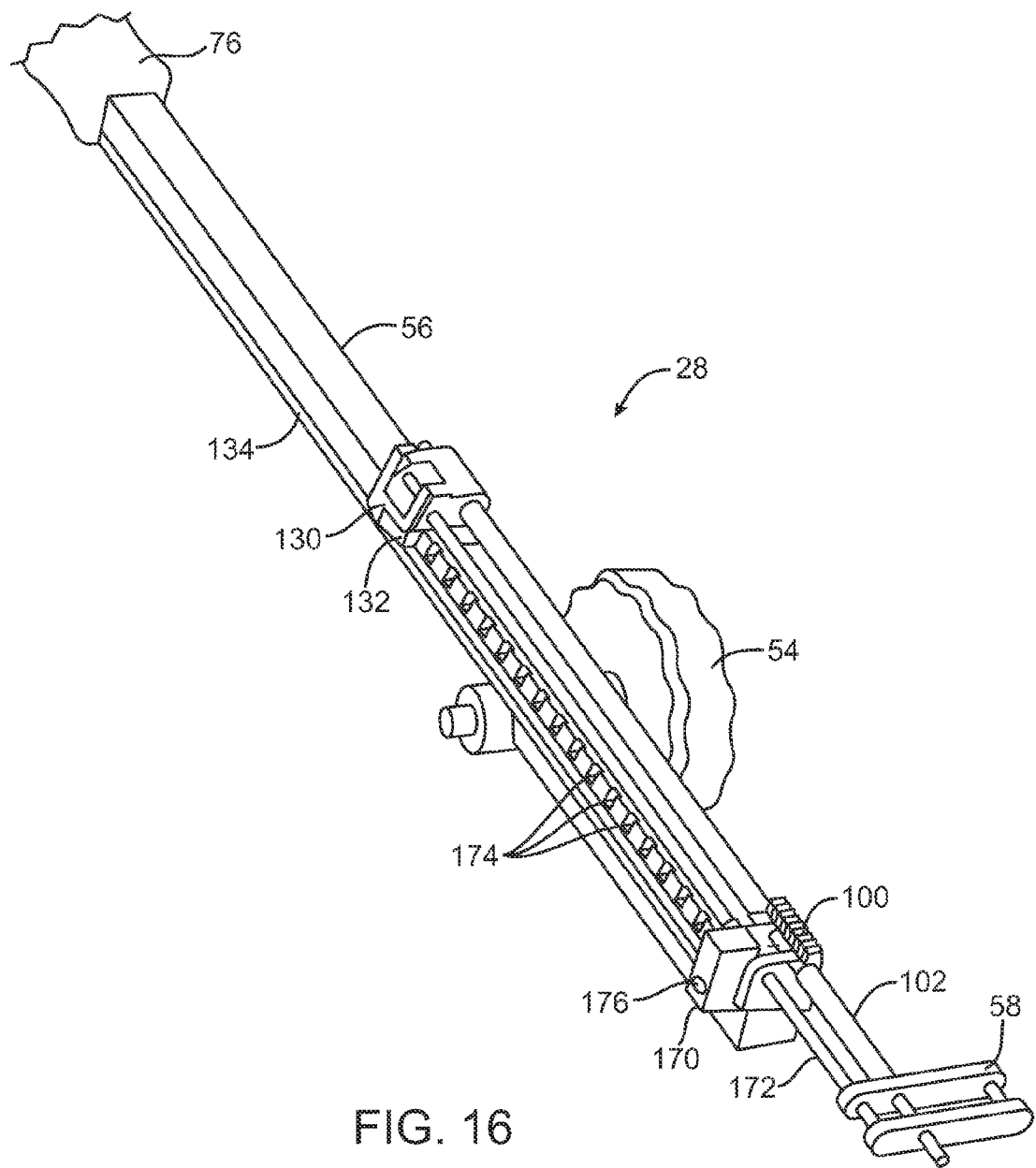
FIG. 16 is an oblique view of the internal components of the handle of the stent delivery catheter of the invention in still another embodiment thereof.

FIG. 16 illustrates a further embodiment of a stent or balloon length indication device according to the invention. The figure illustrates the internal components of handle 28 with handle housing 90 removed, including post 56 to which sheath 38 (not shown) is fixed, brake 100 to which pusher 36 (not shown) is fixed, ratchet frame 130 and pawl 132 that engages rack 134, and actuator knob 54 that drives post 56 distally and proximally. In this embodiment, brake 100 is pivotably coupled to a detent block 170 by an axle 172 extending between ratchet frame 130 and lever 58. Detent block 170 and brake 100 are slidable along axle 172 relative to post 56 to enable positioning of pusher 36 relative to sheath 38. A series of detent slots 174 are disposed in an axial line along the lateral side of post 56 proximal to rack 134. A threaded hole 176 extends through detent block 170 and is configured to receive a detent ball (not shown) sized to engage detent slots 174. A spring (not shown) is inserted in hole 176 behind the detent ball to urge it toward detent slots 174, and a threaded set screw (not shown) is then threaded into hole 176 to hold the spring and detent ball in place. As detent block 170 moves axially relative to post 56, the detent ball engages each detent slot 174 producing an audible click and/or tangible bump detectable by the user. The spacing between each detent slot 174 is selected to be a known distance, e.g., the length of one stent segment 46 or a multiple or fraction thereof. In this way, as the user retracts sheath 38 relative to pusher 36 (and expandable member 30), the user receives an audible or tangible indication of the length of balloon, the length of stent, or the number of stent segments exposed for deployment.

It will be understood that detents and similar features to provide tactile feedback to the user as the length of the interventional element (stent, balloon, etc.) is adjusted may be positioned in various places in the handle or shafts of the interventional catheters of the invention. In still another embodiment, not illustrated, a series of detent holes may be positioned in a circular pattern on the underside of knob 54, and a spring-loaded ball plunger may be mounted to handle 28 in alignment with the detent holes so as to be received therein as knob 54 is rotated. In this way, the user will feel a "bump" or "click" each time the ball plunger engages one of the detent holes. Again, the spacing of the detent holes may be selected to correspond with a known distance such as the length of one of stent segments 46 to provide an indication of the length of the interventional element as it is exposed for deployment.

Figure 17:
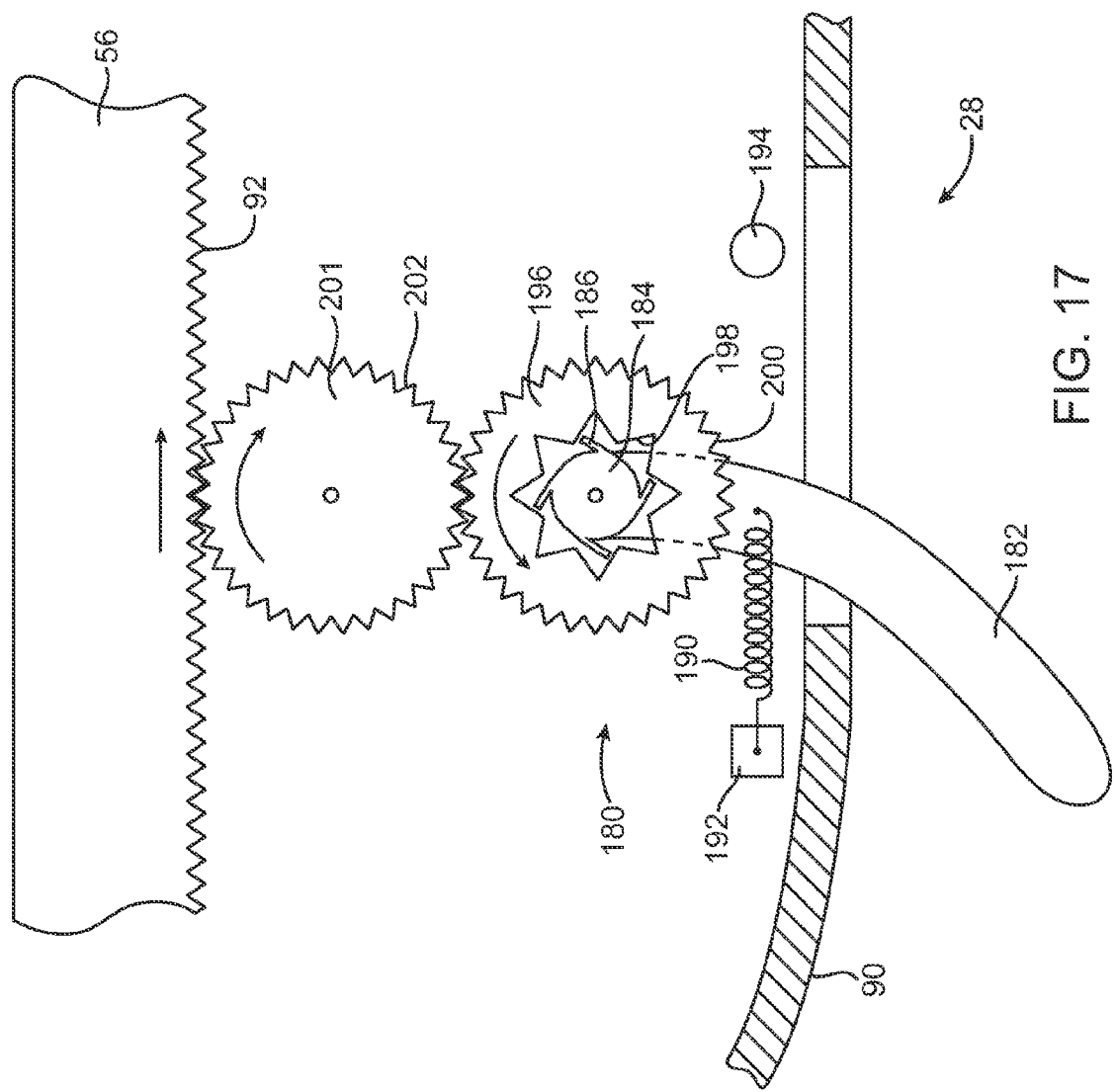
FIG. 17 is a cutaway view of the interior of the handle of a stent delivery catheter according to the invention in a further embodiment thereof.

FIG. 17 illustrates a further embodiment of the invention employing an actuator 180 having a limited stroke such that each actuation exposes a preselected length of a balloon, stent or other interventional element. Actuator 180 comprises a trigger 182 pivotably coupled to handle housing 90. A ratchet wheel 184 is fixed to trigger 182 so as to rotate therewith, and has a plurality of pawls 186 extending outwardly therefrom. Pawls 186 are resiliently deflectable radially inwardly. A spring 190 extending between trigger 182 and block 192 on handle housing 90 biases trigger 182 distally. A stop 194 on handle housing 90 limits the proximal motion of trigger 182. A lower gear 196 is concentrically mounted over ratchet wheel 184 and has inner one-way teeth 198 and outer teeth 200. An upper gear 201 is rotatably mounted to handle housing 90 and has teeth 202 engaged by outer teeth 200. Teeth 202 mate with rack 92 on post 56 (which is coupled to sheath 38, not shown).

In operation, trigger 182 is pulled proximally by the user, thereby rotating ratchet wheel 184. Pawls 188 engage inner one-way teeth 198, turning lower gear 196 in a counterclockwise direction. Outer teeth 200 engage teeth 202, turning upper gear 201 in a clockwise direction, thereby moving post 56 in a proximal direction relative to handle housing 90. This retracts sheath 38 relative to inflation shaft 34, exposing stent segments 46. The location of stop 194 can be selected so that each stroke of trigger 182 exposes a desired length of balloon or stent. For example, each trigger stroke may correspond to the length of one stent segment 46, allowing the user to actuate the trigger once for each stent segment s/he wishes to deploy. When trigger 182 is released, spring 190 pulls it back in the distal direction and pawls 188 are deflected and slide over inner one-way teeth 198 so that post 56 and sheath 38 remain in the retracted position.

A further embodiment of a ratchet mechanism for one-way deployment of an interventional element according to the invention is illustrated in FIGS. 18A-18C. In this embodiment, a pawl 206 is mounted to handle housing 90 and has a tooth 208 that engages a rack 210 on the underside of knob 54.

Pawl 206 has a flat base 212 mounted to handle housing 90 and a resilient inclined extension 214 to which tooth 208 is mounted. Rack 210 has one-way teeth 211 that allow tooth 208 to slide over them as knob 54 is rotated in a first direction, but that engage tooth 208 and prevent rotation in the opposite direction. A camming bar 216 is mounted over pawl 206 and is axially slidable relative thereto. A thumb pad 218 is mounted to the proximal end of camming bar 216. By exerting distal pressure on thumb pad 218, camming bar 216 slides distally, engaging inclined extension 214 and pushing it downward relative to knob 54. This disengages tooth 208 from rack 210. By retracting camming bar 216, inclined extension 214 recoils toward knob 54 so that tooth 208 again engages rack 210.

It will be understood that various types of mechanisms may be used to provide one-way actuation in the interventional catheter of the invention. In another exemplary embodiment, not illustrated, a unidirectional roller clutch may be used to couple knob 54 to pinion gear 96 (or to a shaft fixed thereto). Such a roller clutch transmits torque in a first direction while overrunning freely in the opposite direction. In this way, when rotated in a first direction knob 54 turns pinion gear 96 thereby retracting sheath 38, but when rotated in the opposite direction knob 54 turns freely without turning pinion gear 96. Suitable unidirectional roller clutches are available from, e.g., Stock Drive Products, www.sdp-si.com.

While the above is a complete description of the preferred embodiments of the invention, it will be appreciated that various alternatives, modifications, additions and substitutions are possible without departing from the scope of the invention, which is defined by the claims.

What is claimed is:

1. A catheter comprising:
an elongated flexible shaft having a distal end and a proximal end;
an interventional element at the distal end, the interventional element having an adjustable length, wherein the interventional element comprises a stent comprising a plurality of discrete unconnected stent segments releasably coupled to the shaft adjacent the distal end thereof;
an actuator at the proximal end for adjusting the length of the interventional element, wherein an actuation of the actuator adjusts the number of discrete stent segments in a deployable portion of the stent, and wherein the actuator controls the length of the deployable portion of the stent, the deployable portion being released from the shaft while an undeployed portion of the stent remains coupled to the shaft; and
a post slidably coupled with the actuator at a distal end of the actuator such that the post is retractable within the actuator; wherein a distal end of the post is disposed externally of the actuator, and wherein a distal portion of the post comprises an indication device for providing a tactile indication of the length of the deployable portion of the stent before deployment of the deployable portion.

2. The catheter of claim 1, wherein the interventional element further comprises a balloon.

3. The catheter of claim 2, further comprising a sheath slidably disposed over the balloon, the actuator being coupled to the sheath to axially reposition the sheath relative to the balloon.

4. The catheter of claim 1, wherein the actuator is movable through a distance correlated with the length.

5. The catheter of claim 1, wherein the actuator is movable through a stroke, each stroke of the actuator adjusting the length a predetermined amount.

6. The catheter of claim 1, wherein the indication device comprises a stop that limits the movement of the actuator.

7. The catheter of claim 1, further comprising a sensor for detecting the number of discrete stent segments of the deployable portion of the interventional element.

8. The catheter of claim 7, wherein the sensor is disposed near a distal end of the shaft.

9. The catheter of claim 7, wherein the sensor is optical.

10. The catheter of claim 7, wherein the sensor is magnetic.

11. The catheter of claim 7, further comprising a display associated with the sensor for displaying an indication of the length.

12. The catheter of claim 1, wherein the actuator provides a visual indication of the length.

13. The catheter of claim 1, wherein the indication device emits an audible indication of the length.

14. The catheter of claim 1, wherein the indication device comprises a plurality of holes and a movable detent, each hole being configured to receive the detent, whereby adjusting the length moves the detent from one hole to another hole.

15. The catheter of claim 14, wherein the reception of the detent in one of the holes provides the tactile indication of the length of the interventional element.

16. The catheter of claim 1, wherein the actuator comprises a ratchet mechanism that allows adjustment of the length in a first direction and prevents adjustment of the length in a second direction.

17. A catheter comprising:
an elongated flexible shaft having a distal end a proximal end;
an expandable member mounted at the distal end of the shaft, the expandable member being expandable to an expanded configuration having an expanded length;
a sheath axially movable relative to the shaft and being positionable around at least a portion of the expandable member to restrain the expansion thereof;
a stent comprising a plurality of discrete unconnected stent segments, the stent segments of the stent releasably positioned over the expandable member;
an actuator at the proximal end for controlling the position of the sheath relative to the expandable member to adjust the expanded length of the expandable member, wherein actuation of the actuator adjusts the number of discrete stent segments in a deployable portion of the stent, and wherein the actuator controls the length of the deployable portion of the stent, the deployable portion being released from the shaft while an undeployed portion of the stent remains coupled to the shaft; and
a post slidably coupled with the actuator such that the post is retractable within the actuator; wherein a distal end of the post is disposed externally of the actuator, and wherein a distal portion of the post comprises an indication device for providing a tactile indication of the expanded length of the deployable portion before deployment thereof.

18. The catheter of claim 17, wherein the actuator is movable through a distance correlated with the expandable length.

19. The catheter of claim 17, wherein the actuator is movable through a stroke, each stroke of the actuator adjusting the expandable length a predetermined amount.

20. The catheter of claim 17, wherein the indication device comprises a stop that limits the movement of the actuator.

21. The catheter of claim 17, further comprising a sensor for detecting the number of discrete stent segments of the deployable portion.

22. The catheter of claim 21, wherein the sensor is disposed near a distal end of the shaft.

23. The catheter of claim 21, wherein the sensor is optical.

24. The catheter of claim 21, wherein the sensor is magnetic.

25. The catheter of claim 21, further comprising a display associated with the sensor for displaying an indication of the length.

26. The catheter of claim 17, wherein the actuator provides a visual indication of the length.

27. The catheter of claim 17, wherein the indication device emits an audible indication of the length.

28. The catheter of claim 17, wherein the indication device comprises a plurality of holes and a movable detent, each hole being configured to receive the detent, whereby adjusting the length moves the detent from one hole to another hole.

29. The catheter of claim 28, wherein the reception of the detent in one of the holes provides the tactile indication of the length of the interventional element.

30. The catheter of claim 17, wherein the actuator comprises a ratchet mechanism that allows adjustment of the length in a first direction and prevents adjustment of the length in a second direction.

31. A stent delivery catheter comprising:
an elongated flexible shaft having distal and proximal ends;
a stent comprising a plurality of discrete unconnected stent segments releasably mounted at the distal end, a deployable portion of the stent being releasable from the catheter to assume an expanded configuration, the deployable portion having a length and comprising one or more stent segments;
an actuator at the proximal end for controlling the length of the deployable portion, wherein actuation of the actuator adjusts the number of discrete stent segments in the deployable portion, and wherein the actuator controls the length of the deployable portion of the stent, the deployable portion being released from the shaft while an undeployed portion of the stent remains coupled to the shaft; and
a post slidably coupled with the actuator such that the post is retractable within the actuator; wherein a distal end of the post is disposed externally of the actuator, and wherein a distal portion of the post comprises an indication device for tactilely indicating the length of the deployable portion before deployment of the deployable portion.

32. The catheter of claim 31, wherein the actuator is movable through a distance correlated with the length.

33. The catheter of claim 31, wherein the actuator is movable through a stroke, each stroke of the actuator adjusting the length a predetermined amount.

34. The catheter of claim 33, wherein the stent comprises a plurality of stent segments, and the stroke corresponds to a segment length of one of the stent segments.

35. The catheter of claim 31, wherein the indication device comprises a stop that limits the movement of the actuator.

36. The catheter of claim 31, further comprising a sensor for detecting the number of discrete stent segments of the deployable portion.

37. The catheter of claim 36, wherein the sensor is disposed near a distal end of the shaft.

38. The catheter of claim 36, wherein the sensor is optical.

39. The catheter of claim 36, wherein the sensor is magnetic.

40. The catheter of claim 36, further comprising a display associated with the sensor for displaying an indication of the length.

41. The catheter of claim 31, wherein the actuator provides a visual indication of the length.

42. The catheter of claim 31, wherein the indication device emits an audible indication of the length.

43. The catheter of claim 31, wherein the indication device comprises a plurality of holes and a movable detent, each hole being configured to receive the detent, whereby adjusting the length moves the detent from one hole to another hole.

44. The catheter of claim 43, wherein the reception of the detent in one of the holes provides the tactile indication of the length of the interventional element.

45. The catheter of claim 31, wherein the actuator comprises a ratchet mechanism that allows adjustment of the length in a first direction and prevents adjustment of the length in a second direction.

46. The catheter of claim 31, wherein the catheter further comprises a sheath slidable relative to the stent segments for selectively covering a first portion of the stent segment and exposing a second portion of the stent segments.

47. The catheter of claim 46, wherein the actuator moves the sheath relative to the stent segments.

48. The catheter of claim 31, wherein the actuator is further adapted to axially separate a first stent segment from a second stent segment prior to expansion thereof.

49. The catheter of claim 48, wherein the actuator is adapted to separate the first and second stent segments by a predetermined distance.

50. The catheter of claim 48, wherein the actuator has a first position for controlling the number of stent segments in the deployable portion and a second position for controlling the separation between the first and second stent segments.

51. The catheter of claim 31, wherein the indication device indicates a number of stent segments in the deployable portion.

52. The catheter of claim 31, wherein the indication device indicates the length of the undeployed portion.

* * * * *